(12) United States Patent
Min et al.

(10) Patent No.: US 11,794,022 B2
(45) Date of Patent: Oct. 24, 2023

(54) SYSTEMS AND METHODS FOR PERFORMING PACING USING MULTIPLE LEADLESS PACEMAKERS

(71) Applicant: Pacesetter, Inc., Sylmar, CA (US)

(72) Inventors: Xiaoyi Min, Santa Rosa Valley, CA (US); Matthew G. Fishler, Scotts Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 220 days.

(21) Appl. No.: 17/330,684

(22) Filed: May 26, 2021

(65) Prior Publication Data
US 2021/0290965 A1    Sep. 23, 2021

Related U.S. Application Data

(63) Continuation of application No. 16/241,397, filed on Jan. 7, 2019, now Pat. No. 11,071,872.

(51) Int. Cl.
*A61N 1/375* (2006.01)
*A61N 1/39* (2006.01)
(Continued)

(52) U.S. Cl.
CPC ......... *A61N 1/3756* (2013.01); *A61N 1/3682* (2013.01); *A61N 1/3688* (2013.01); *A61N 1/37512* (2017.08); *A61N 1/39622* (2017.08); *A61B 5/686* (2013.01); *A61N 1/3684* (2013.01); *A61N 1/37252* (2013.01)

(58) Field of Classification Search
CPC .. A61N 1/3756; A61N 1/3682; A61N 1/3688; A61N 1/37512; A61N 1/39622; A61N 1/3684; A61N 1/37252; A61N 1/36521; A61N 1/36578; A61N 1/368;
(Continued)

(56) References Cited

U.S. PATENT DOCUMENTS 8,386,049 B2    2/2013  Persson et al.
8,554,333 B2   10/2013  Wu et al.
(Continued)

OTHER PUBLICATIONS

Non-final Office Action dated Jun. 12, 2020, U.S. Appl. No. 16/241,397, filed Jan. 7, 2019.
(Continued)

*Primary Examiner* — Gary Jackson
*Assistant Examiner* — Alexander M Eisenberg
(74) *Attorney, Agent, or Firm* — Vierra Magen Marcus LLP

(57) ABSTRACT

An implantable system includes a first leadless pacemaker (LP1) implanted in or on a first chamber of a heart and a second leadless pacemaker (LP2) implanted in or on a second chamber of the heart. The LP1 is configured to time delivery of one or more pacing pulses delivered to the first chamber of the heart based on timing of cardiac activity associated with the second chamber of the heart detected by the LP1 itself. The LP1 is also configured to transmit implant-to-implant (i2i) messages to the LP2. The LP2 is configured to time delivery of one or more pacing pulses delivered to the second chamber of the heart based on timing of cardiac activity associated with the second chamber of the heart as determined based on one or more i2i messages received by the LP2 from the LP1.

22 Claims, 12 Drawing Sheets

(51) Int. Cl.
*A61N 1/368* (2006.01)
*A61N 1/372* (2006.01)
*A61B 5/00* (2006.01)

(58) Field of Classification Search
CPC . A61N 1/37288; A61N 1/36507; A61B 5/686
See application file for complete search history.

(56) References Cited

U.S. PATENT DOCUMENTS

| | | | |
|---|---|---|---|
| 8,923,963 | B2 | 12/2014 | Bonner et al. |
| 8,996,109 | B2 | 3/2015 | Karst et al. |
| 9,457,193 | B2 | 10/2016 | Klimovitch et al. |
| 9,522,280 | B2 | 12/2016 | Fishler et al. |
| 9,561,382 | B2 | 2/2017 | Persson et al. |
| 9,889,303 | B2 | 2/2018 | Brown et al. |
| 2009/0275998 | A1* | 11/2009 | Burnes .................. A61N 1/368 607/4 |
| 2010/0121394 | A1* | 5/2010 | Gill ........................ A61B 5/349 607/9 |
| 2013/0123875 | A1 | 5/2013 | Varady et al. |
| 2014/0100627 | A1 | 4/2014 | Min |
| 2015/0224320 | A1 | 8/2015 | Stahmann |
| 2016/0015287 | A1 | 1/2016 | Anderson et al. |
| 2016/0121128 | A1* | 5/2016 | Fishler ................. H04W 52/04 607/32 |
| 2016/0206892 | A1* | 7/2016 | Demmer ............ A61N 1/37288 |
| 2016/0296760 | A1 | 10/2016 | Sahabi et al. |
| 2018/0008831 | A1 | 1/2018 | An et al. |
| 2018/0028821 | A1 | 2/2018 | Starke et al. |
| 2018/0085589 | A1 | 3/2018 | Splett et al. |
| 2018/0126161 | A1 | 5/2018 | Chin et al. |
| 2019/0184181 | A1* | 6/2019 | Zhao .................. A61N 1/37217 |
| 2019/0201696 | A1 | 7/2019 | Koop et al. |
| 2020/0086129 | A1 | 3/2020 | Min et al. |
| 2020/0215336 | A1 | 7/2020 | Min et al. |
| 2020/0215337 | A1 | 7/2020 | Min et al. |
| 2020/0215341 | A1 | 7/2020 | Min et al. |

OTHER PUBLICATIONS

Response to Office Action dated Aug. 28, 2020, U.S. Appl. No. 16/241,397, filed Jan. 7, 2019.
Final Office Action dated Nov. 6, 2020, U.S. Appl. No. 16/241,397, filed Jan. 7, 2019.
Response to Office Action dated Jan. 15, 2021, U.S. Appl. No. 16/241,397.
Notice of Allowance dated May 3, 2021, U.S. Appl. No. 16/241,397, filed Jan. 7, 2019.
Final Office Action dated May 6, 2021, U.S. Appl. No. 16/241,378, filed Jan. 7, 2019.
Response to Office Action dated May 21, 2021, U.S. Appl. No. 16/241,378, filed Jan. 7, 2019.
Kurcheti, Krishna K., "Understanding and Implementing Different Modes of Pacemaker," Master of Science Report, Department of Computing and Information Sciences, Vignan Engineering College, Kansas State University, Jul. 2012, 66 pages.
Benson, Regina MD, "Pacemaker Nomenclature," Key Word Project, 2005-2006 Academic Year, Oct. 2005, 2 pages.
Non-final Office Action dated Jan. 13, 2021, U.S. Appl. No. 16/241,378, filed Jan. 7, 2019.
Response to Office Action dated Apr. 9, 2021, U.S. Appl. No. 16/241,378, filed Jan. 7, 2019.
Restriction Requirement dated Jun. 10, 2020, U.S. Patent Application No. 16/241,389, filed Jan. 7, 2019.
Response to Restriction Requirement dated Jun. 19, 2020, U.S. Appl. No. 16/241,389, filed Jan. 7, 2019.
Non-final Office Action dated Jul. 24, 2020, U.S. Patent Application No. 16/241,389 filed Jan. 7, 2019.
Response to Office Action dated Sep. 25, 2020, U.S. Appl. No. 16/241,389, filed Jan. 7, 2019.
Non-final Office Action dated Dec. 18, 2020, U.S. Appl. No. 16/241,389, filed Jan. 7, 2019.
Response to Office Action dated Jan. 11, 2021, U.S. Appl. No. 16/241,389, filed Jan. 7, 2019.
Final Office Action dated Mar. 30, 2021, U.S. Appl. No. 16/241,389, filed Jan. 7, 2019.

* cited by examiner

SYSTEMS AND METHODS FOR PERFORMING PACING USING MULTIPLE LEADLESS PACEMAKERS

PRIORITY CLAIM

This application is a continuation, of and claims priority to, U.S. patent application Ser. No. 16/241,397, filed Jan. 7, 2019, which issued as U.S. Pat. No. 11,071,872 on Jul. 27, 2021, and which is incorporated herein by reference.

FIELD OF TECHNOLOGY

Embodiments described herein generally relate to methods and systems for performing various types of pacing using leadless pacemakers, as well as various leadless pacemaker embodiments and methods for use therewith.

BACKGROUND

Some cardiac pacing systems include one or more leadless pacemakers (LPs). Such an LP of a cardiac pacing system can be used to deliver pacing pulses to a cardiac chamber within (or on) which the LP is implanted. In order to know when to deliver its pacing pulses, an LP may need to determine cardiac activity associated with another cardiac chamber. For an example, in order for an LP implanted in (or on) the right ventricular (RV) chamber to know when to deliver pacing pulses to the RV chamber, the LP may need to determine cardiac activity associate with the right atrial (RA) chamber, e.g., in order to achieve a desired atrioventricular (AV) delay. For another example, in order for an LP implanted in (or on) the RA chamber to know when to deliver pacing pulses to the RA chamber, the LP may need to determine cardiac activity associate with the RV chamber, e.g., in order to achieve a desired VA interval.

There are various different ways that an LP can determine cardiac activity associated with another cardiac chamber, in order to known when to delivers its pacing pulses. For example, an LP implanted within or on a cardiac chamber can perform implant-to-implant (i2i) communication with another LP that is implanted within or on another cardiac chamber, or the LP can sense a far-field signal indicative of cardiac activity in another chamber. Such i2i communication can involve one LP implanted in a cardiac chamber informing another LP implanted in another cardiac chamber of a paced or sensed event, so that coordinated synchronous pacing can be performed in multiple cardiac chambers. While such techniques are generally known, it would be beneficial to improve such techniques, e.g., to provide for improved pacing, improved i2i communication, and/or improved far-field sensing. Further, it would be beneficial to provide new and improved LPs that can be used to perform such techniques.

SUMMARY

Certain embodiments of the present technology are related to implantable systems and methods for use therewith. Such an implantable system can include a first leadless pacemaker (LP1) configured to be implanted in or on a first chamber of a heart, and a second leadless pacemaker (LP2) configured to be implanted in or on a second chamber of the heart. The LP1 is configured to time delivery of one or more pacing pulses delivered to the first chamber of the heart based on timing of cardiac activity associated with the second chamber of the heart detected by the LP1 itself. The LP1 is also configured to transmit implant-to-implant (i2i) messages to the LP2. The LP2 is configured to time delivery of one or more pacing pulses delivered to the second chamber of the heart based on timing of cardiac activity associated with the second chamber of the heart as determined based on one or more i2i messages received by the LP2 from the LP1. In certain embodiments, the LP1 is configured to be implanted in or on a right ventricular (RV) chamber, and the LP2 is configured to be implanted in or on a right atrial (RA) chamber. In other embodiments, the LP1 is configured to be implanted in or on a RA chamber, and the LP2 is configured to be implanted in or on a RV chamber.

In accordance with certain embodiments, the LP1 is configured to obtain a far-field signal from which electrical cardiac activity associated with the second chamber of the heart may be detected, and use the far-field signal to thereby time delivery of one or more pacing pulses delivered to the first chamber of the heart, based on timing of cardiac activity associated with the second chamber of the heart detected by the LP1 itself from the far-field signal. In certain such embodiments, the LP1 is configured to be implanted in or on the RV chamber, and the LP2 is configured to be implanted in or on the RA chamber. Alternatively, the LP1 is configured to be implanted in or on the RA chamber, and the LP2 is configured to be implanted in or on the RV chamber.

In accordance with certain embodiments, the LP1 is configured to obtain a sensor signal from which mechanical cardiac activity associated with the second chamber of the heart may be detected, and use the sensor signal to thereby time delivery of one or more pacing pulses delivered to the first chamber of the heart, based on timing of cardiac activity associated with the second chamber of the heart detected by the LP1 itself from the sensor signal. In certain such embodiments, the LP1 is configured to be implanted in or on the RV chamber, and the LP2 is configured to be implanted in or on the RA chamber. Alternatively, the LP1 is configured to be implanted in or on the RA chamber, and the LP2 is configured to be implanted in or on the RV chamber.

In accordance with certain embodiments, the LP1 is configured to be implanted in or on a RA chamber and the LP2 is configured to be implanted in or on a RV chamber. The LP1 is configured to perform at least one of AAI, ADI or ADD pacing, the LP2 is configured to perform at least one of VVI, VDI or VDD pacing, and the LP1 and the LP2 collectively provide DDD or DDI pacing or some other dual chamber pacing mode that provides synchronization between the LP1 and the LP2.

In accordance with other embodiments, the LP1 is configured to be implanted in or on a RV chamber, and the LP2 is configured to be implanted in or on a RA chamber. The LP1 is configured to perform at least one of VVI, VDI or VDD pacing, the LP2 is configured to perform at least one of AAI, ADI or ADD pacing, and the LP1 and the LP2 collectively provide DDD or DDI pacing or some other dual chamber pacing mode that provides synchronization between the LP1 and the LP2.

Certain embodiments of the present technology are related to methods for use with an implantable system including a first leadless pacemaker (LP1) configured to be implanted in or on a first chamber of a heart, and a second leadless pacemaker (LP2) configured to be implanted in or on a second chamber of the heart. Such a method can include the LP1 timing delivery of one or more pacing pulses delivered to the first chamber of the heart based on timing of cardiac activity associated with the second chamber of the heart detected by the LP1 itself, and the LP1 transmitting implant-to-implant (i2i) messages to the LP2. Such a method can further include the LP2 timing delivery of one or more pacing pulses delivered to the second chamber of the heart based on timing of cardiac activity associated with the second chamber of the heart as determined based on one or more i2i messages received by the LP2 from the LP1.

In accordance with certain embodiments, wherein the LP1 is configured to be implanted in or on a RV chamber and the LP2 is configured to be implanted in or on a RA chamber, the LP1 timing delivery of one or more pacing pulses delivered to the first chamber of the heart comprises the LP1 timing delivery of one or more pacing pulses delivered to the RV chamber based on timing of cardiac activity associated with the RA chamber detected by the LP1 itself. In such embodiments, the LP2 timing delivery of one or more pacing pulses delivered to the second chamber of the heart comprises the LP2 timing delivery of one or more pacing pulses delivered to the RA chamber based on timing of cardiac activity associated with the RV chamber as determined based on one or more i2i messages received by the LP2 from the LP1.

In accordance with certain embodiments, wherein the LP1 is configured to be implanted in or on a RA chamber and the LP2 is configured to be implanted in or on a RV chamber, the LP1 timing delivery of one or more pacing pulses delivered to the first chamber of the heart comprises the LP1 timing delivery of one or more pacing pulses delivered to the RA chamber based on timing of cardiac activity associated with the RV chamber detected by the LP1 itself. In such embodiments, the LP2 timing delivery of one or more pacing pulses delivered to the second chamber of the heart comprises the LP2 timing delivery of one or more pacing pulses delivered to the RV chamber based on timing of cardiac activity associated with the RA chamber as determined based on one or more i2i messages received by the LP2 from the LP1.

In accordance with certain embodiments, the LP1 timing delivery of one or more pacing pulses delivered to the first chamber of the heart comprises the LP1 obtaining a far-field signal from which electrical cardiac activity associated with the second chamber of the heart may be detected, and the LP1 using the far-field signal to thereby time delivery of one or more pacing pulses delivered to the first chamber of the heart, based on timing of cardiac activity associated with the second chamber of the heart detected by the LP1 itself from the far-field signal. In certain such embodiments, wherein the LP1 is configured to be implanted in or on the RV chamber and the LP2 is configured to be implanted in or on the RA chamber, the LP1 obtaining a far-field signal comprises the LP1 obtaining a far-field signal from which electrical cardiac activity associated with the RA chamber may be detected, and the LP1 using the far-field signal comprises the LP1 using the far-field signal to thereby time delivery of one or more pacing pulses delivered to the RV chamber, based on timing of cardiac activity associated with the RA chamber detected by the LP1 itself from the far-field signal. In alternative such embodiments, wherein the LP1 is configured to be implanted in or on the RA chamber and the LP2 is configured to be implanted in or on the RV chamber, the LP1 obtaining a far-field signal comprises the LP1 obtaining a far-field signal from which electrical cardiac activity associated with the RV chamber may be detected, and the LP1 using the far-field signal comprises the LP1 using the far-field signal to thereby time delivery of one or more pacing pulses delivered to the RA chamber, based on timing of cardiac activity associated with the RV chamber detected by the LP1 itself from the far-field signal.

In accordance with certain embodiments, the LP1 timing delivery of one or more pacing pulses delivered to the first chamber of the heart comprises the LP1 obtaining a sensor signal from which mechanical cardiac activity associated with the second chamber of the heart may be detected, and the LP1 using the sensor signal to thereby time delivery of one or more pacing pulses delivered to the first chamber of the heart, based on timing of cardiac activity associated with the second chamber of the heart detected by the LP1 itself from the sensor signal. In certain such embodiments, wherein the LP1 is configured to be implanted in or on a RV chamber and the LP2 is configured to be implanted in or on a RA chamber, the LP1 obtaining a sensor signal comprises the LP1 obtaining a sensor signal from which mechanical cardiac activity associated with the RA chamber may be detected, and the LP1 using the sensor signal comprises the LP1 using the sensor signal to thereby time delivery of one or more pacing pulses delivered to the RV chamber, based on timing of cardiac activity associated with the RA chamber detected by the LP1 itself from the sensor signal. In alternative such embodiments, wherein the LP1 is configured to be implanted in or on a RA chamber and the LP2 is configured to be implanted in or on a RV chamber, the LP1 obtaining a sensor signal comprises the LP1 obtaining a sensor signal from which mechanical cardiac activity associated with the RV chamber may be detected, and the LP1 using the sensor signal comprises the LP1 using the sensor signal to thereby time delivery of one or more pacing pulses delivered to the RA chamber, based on timing of cardiac activity associated with the RV chamber detected by the LP1 itself from the sensor signal.

Certain embodiments of the present technology are directed to an implantable system that includes a first leadless pacemaker (LP1) configured to be implanted in or on a RA chamber, and a second leadless pacemaker (LP2) configured to be implanted in or on a RV chamber, wherein the LP1 is configured to perform at least one of AAI, ADI or ADD pacing, the LP2 is configured to perform at least one of VVI, VDI or VDD pacing, and the LP1 and the LP2 collectively provide DDD or DDI pacing or some other dual chamber pacing mode that provides synchronization between the LP1 and the LP2. Where two LPs (e.g., the LP1 and the LP2) are said to be synchronized or have synchronization provided, this means that the pacing performed by at least one of the LPs is timed relative to paced events delivered by and/or sensed events sensed by the other one of the LPs. Accordingly, two LPs can be said to be synchronized where there is VA synchrony but not AV synchrony, VA synchrony but not AV synchrony, or both VA and AV synchrony This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Figure 1A:
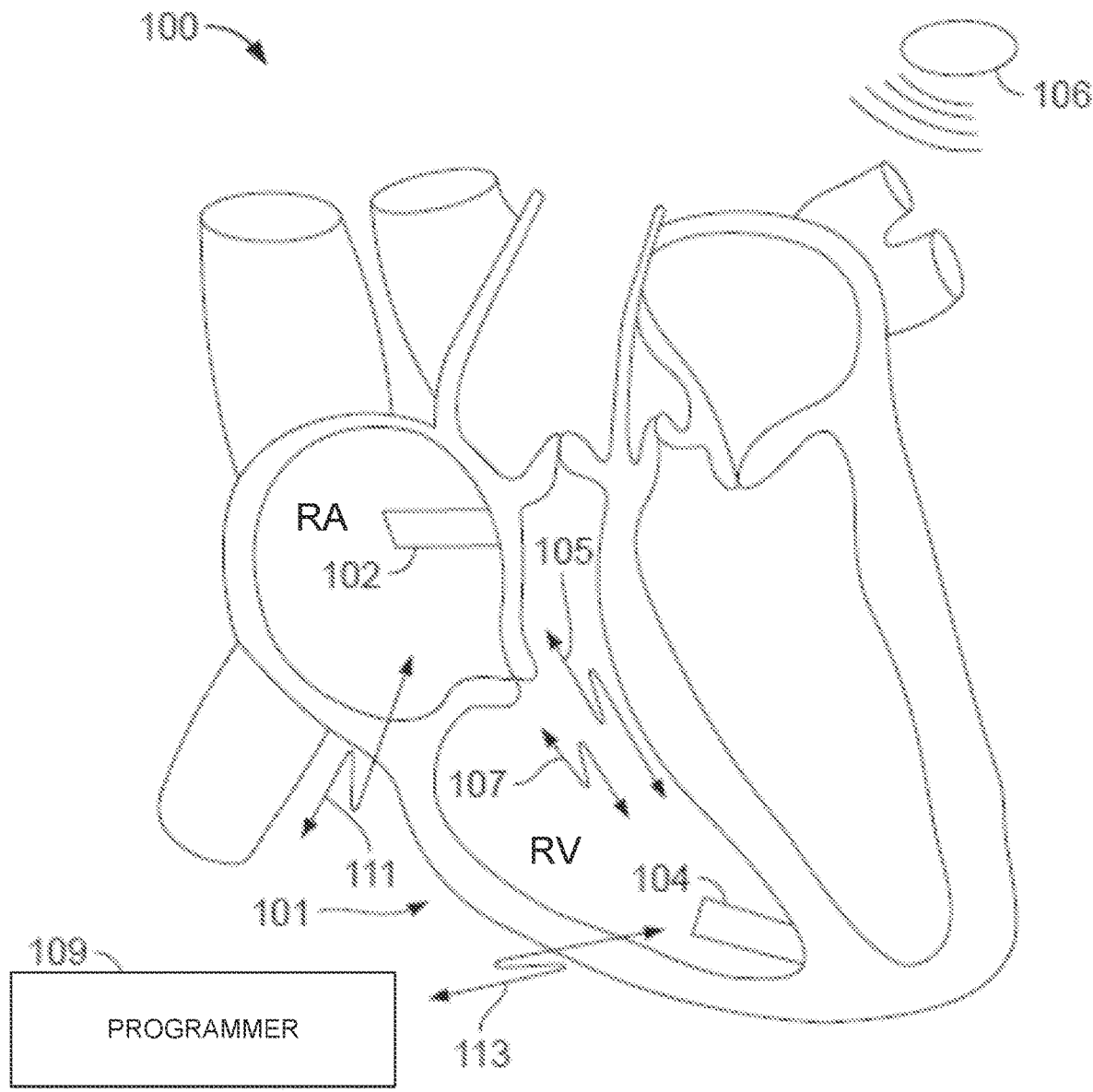
FIG. 1A illustrates a system formed in accordance with certain embodiments described herein as implanted in a heart.

Certain embodiments of the present technology relate to implantable systems, and methods for use therewith, that can be used to perform various pacing schemes using one or more LPs. For example, certain embodiments of the present technology relate to implantable systems, and methods for use therewith, that can be used perform DDD pacing using two LPs. More specifically, in accordance with certain embodiments of the present technology, an LP is implanted in (or on) a patient's RV chamber and is used to perform VDD pacing, and another LP is implanted in (or on) the patient's RA chamber and is used to perform ADD, AAI, or ADI pacing. Collectively, the two LPs are used to perform DDD or DDI pacing or some other dual chamber pacing mode that provides synchronization between the LP1 and the LP2. Where two LPs (e.g., the LP1 and the LP2) are said to be synchronized or have synchronization provided, this means that the pacing performed by at least one of the LPs is timed relative to paced events delivered by and/or sensed events sensed by the other one of the LPs. Accordingly, two LPs can be said to be synchronized where there is VA synchrony but not AV synchrony, VA synchrony but not AV synchrony, or both VA and AV synchrony Any one of various different algorithms can be used to achieve such dual chamber pacing modes. When referring to various types of pacing schemes herein, three letters are often used to refer to the type of pacing. In other words, a three position pacemaker code is often used, with the following nomenclature followed: the first position refers to the cardiac chamber paced; the second position refers to the cardiac chamber sensed; and the third position refers to the response to a sensed event. In the first and second positions, the letter O means none, the letter A means Atrium, the letter V means Ventricle, and the letter D means Dual (i.e., A and V). In the third position the letter O means none, the letter I means Inhibited, the letter T means Triggered (aka Tracked), and the letter D means Dual (i.e., T+I). The below Table 1 summarizes this pacemaker nomenclature.

TABLE 1

| Position 1 (Chamber Paced) | Position 2 (Chamber Sensed) | Position 3 (Response to Sensed Event) |
| --- | --- | --- |
| O = none | O = none | O = none |
| A = Atrium | A = Atrium | I = Inhibited |
| V = Ventricle | V = Ventricle | T = Triggered (aka Tracked) |
| D = Dual (A + V) | D = Dual (A + V) | D = Dual (I + T) |

Accordingly, if an LP in the patient's RV chamber performs VDD pacing, that means it paces only the RV chamber, senses both atrial and ventricular activity, and inhibits pacing of the RV if a sensed event is detected within a specified interval (the AV interval) or triggers pacing of the RV at the end of the specified interval (the AV interval) if a sensed event is not detected within that specified interval (the AV interval). For another example, if an LP in the patient's RA chamber performs AAI pacing, that means it paces only the RA chamber, senses only atrial activity, and inhibits pacing of the RA chamber if a sensed event is detected within a specified interval. Where the second position includes a "D", the LP will need to be aware of activity in its own chamber and in another chamber in or one which the LP is not implanted. Activity in another chamber can be determined from a far-field signal and/or from an i2i message received from another LP that is in or one the other chamber.

The LP in (or on) the patient's RA chamber can also be referred to as the aLP, and the LP in (or on) the patient's RV chamber can also be referred to as the vLP. There are various different ways that an external programmer can instruct an aLP and an vLP to perform certain pacing modes that are the equivalent of pacing modes performed using conventional (i.e., non-leadless) pacemakers. For example, assume that it is desired that an aLP performs one of ADD, AAI, or ADI pacing, and the vLP performs VDD pacing, such that collectively the aLP and the vLP perform DDD or DDI pacing. The external programmer can instruct the aLP to perform a specific one of ADD, AAI, or ADI pacing, and external programmer can instruct the vLP to perform VDD pacing. Alternatively, the external programmer can instruct both of the aLP and the vLP to perform DDD or DDI pacing, in response to which the aLP will know (based on how it is programmed) to perform a specific one of ADD, AAI, or ADI pacing, and the vLP will know (based on how it is programmed) to perform VDD pacing, such that collectively the aLP and the vLP will perform DDD or DDI pacing. Other variations are also possible.

When the LP in (or on) the RV chamber performs VDD pacing, it should know when certain cardiac activity (e.g., atrial contractions) occur in the RA chamber, so that it knows the appropriate times at which to pace the RV chamber. In accordance with certain embodiments, the LP in (or on) the RV chamber senses a far-field signal from which electrical cardiac activity associated with the RA chamber may be detected, and the LP in (or on) the RV chamber times its delivery of RV pacing pulses based on the timing of the electrical cardiac activity associated with the RA chamber detected from the far-field signal. For example, the LP in the RV chamber may be able to detect P waves from the far-field signal it senses in order to know when to deliver RV pacing pulses. The LP in the RV chamber can alternatively or additionally determine the timing of atrial cardiac activity based on i2i messages received from an LP implanted in the RA chamber. As will be described in additionally detail below, delivery of an i2i message from the LP in the RA chamber (to the LP in the RV chamber) can be via pulses generated by the LP in the RA chamber in response to a sensed or paced atrial event, wherein such pulses can be generated (and thus delivered) prior to, during, or after an atrial refractor period associated with the atrial event, depending upon implementation. The LP in the RV chamber can alternatively or additionally use a sensor (e.g., an accelerometer or a pressure sensor) to produce a sensor signal from which the LP in the RV chamber can detect cardiac mechanical activity associated with the RA chamber, and time its RV pacing pulses based thereon. Combinations of these aforementioned embodiments are also described herein.

In certain embodiments, the LP in (or on) the RV chamber primarily relies on far-field sensing of electrical cardiac activity associated with the RA chamber to time delivery of RV pacing pulses, but uses i2i messaging as a backup. In alternative embodiments, the LP in (or on) the RV chamber primarily times delivery of RV pacing pulses based on the timing of cardiac activity associated with the RA chamber as determined from i2i messages, and uses far-field sensing as backup. Other variations are also possible and within the scope of the embodiments described herein.

When the LP in (or on) the RA chamber performs ADD pacing, it should know when certain cardiac activity (e.g., ventricular contractions) occur in the RV chamber, so that it knows the appropriate times at which to pace the RA chamber. In accordance with certain embodiments, the LP in (or on) the RA chamber senses a far-field signal from which electrical cardiac activity associated with the RV chamber may be detected, and the LP in (or on) the RA chamber times its delivery of RA pacing pulses based on the timing of the electrical cardiac activity associated with the RV chamber detected from the far-field signal. For example, the LP in the RA chamber may be able to detect R waves from the far-field signal it senses in order to know when to deliver RA pacing pulses. The LP in the RA chamber can alternatively or additionally determine the timing of ventricular cardiac activity based on i2i messages received from an LP implanted in the RV chamber. The LP in the RA chamber can alternatively or additionally use a sensor (e.g., an accelerometer or a pressure sensor) to produce a sensor signal from which the LP in the RA chamber can detect cardiac mechanical activity associated with the RV chamber, and time its RA pacing pulses based thereon. Combinations of these aforementioned embodiments are also described herein.

In certain embodiments, the LP in (or on) the RA chamber primarily relies on far-field sensing of electrical cardiac activity associated with the RV chamber to time delivery of RA pacing pulses, but uses i2i messaging as a backup. In alternative embodiments, the LP in (or on) the RA chamber primarily times delivery of RA pacing pulses based on the timing of cardiac activity associated with the RV chamber as determined from i2i messages, and uses far-field sensing as backup. Other variations are also possible and within the scope of the embodiments described herein.

In certain embodiments, the LP in (or on) the RV chamber performs VVI pacing (e.g., using programmed VV intervals), and the LP in (or on) the RA chamber performs ADD or ADI pacing. The ADD or ADI pacing performed by the LP in (or on) the RA chamber can involve pacing and sensing in the RA chamber, sensing in the RV chamber (achieved by sensing a far-field signal, or producing a sensor signal from which mechanical cardiac activity in the RV chamber can be detected). Such a system would be useful for patients having sinus rhythm with heart block and intermittent atrial arrhythmia. An advantage of this system is that it could achieve dual chamber pacing and sensing with only one of LPs obtaining a far-field signal indicative of ventricular cardiac activity (which is much stronger than a far-field signal indicative of atrial cardiac activity).

In certain embodiments, the LP in (or on) the RV chamber performs VDI pacing (e.g., using programmed VV and VA intervals), and the LP in (or on) the RA chamber performs AAI pacing. Such a system essentially provides for DDI pacing.

Before providing addition details of the specific embodiments of the present technology mentioned above, as well as additional embodiments of the present technology, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more LPs, an implantable cardioverter-defibrillator (ICD), such as a subcutaneous-ICD, and/or a programmer reliably and safely coordinate pacing and/or sensing operations. Later on, specific embodiments of LPs according to certain embodiments of the present technology will be described, e.g., with reference to FIGS. 9A and 9B.

FIG. 1A illustrates a system 100 formed in accordance with certain embodiments herein as implanted in a heart 101. The system 100 comprises two or more LPs 102 and 104 located in different chambers of the heart. LP 102 is located in the RA chamber, while LP 104 is located in the RV chamber. LPs 102 and 104 can communicate with one another to inform one another of various local physiologic activities, such as local intrinsic events, local paced events and the like. LPs 102 and 104 may be constructed in a similar manner, but operate differently based upon which chamber LP 102 or 104 is located. It is noted that the RA chamber is also known as the right atrium, and the acronym RA can be used to refer to the "right atrium" or to refer to the "right atrial" chamber. Similarly, the RV chamber is also known as the right ventricle, and the acronym RV can be used to refer to the "right ventricle" or to refer to the "right ventricular" chamber. It is also noted that the terms "cardiac chamber", "chamber of the heart", and "chamber of a patient's heart" are used interchangeably herein.

In accordance with certain embodiments, the LP 102 is used to perform ADD pacing, the LP 104 is used to perform VDD pacing, and the LPs 102 and 104 are collectively used to perform DDD pacing. The ADD pacing (performed by the LP 102) involves atrial pacing, ventricular and atrial (i.e., dual) sensing, and dual (i.e., triggered and inhibited) response to a sensed event. The VDD pacing (performed by the LP 104) involves ventricular pacing, atrial and ventricular (i.e., dual) sensing, and dual (i.e., triggered and inhibited) response to a sensed event. The DDD pacing (performed collectively by the LPs 102 and 104) involves atrial and ventricular (i.e., dual) pacing, atrial and ventricular (i.e., dual) sensing, and dual (i.e., triggered and inhibited) response to a sensed event.

In some embodiments, LPs 102 and 104 communicate with one another, with an ICD 106, and with an external device (e.g., programmer) 109 through wireless transceivers, communication coils and antenna, and/or by conductive communication through the same electrodes as (or one or more different electrodes than) used for sensing and/or delivery of pacing therapy. When conductive communication is performed using electrodes, the system 100 may omit an antenna or telemetry coil in one or more of LPs 102 and 104.

In some embodiments, one or more LPs 102 and 104 can be co-implanted with the ICD 106. Each LP 102, 104 uses two or more electrodes located within, on, or within a few centimeters of the housing of the LP, for pacing and sensing at the cardiac chamber, for bidirectional communication with one another, with the programmer 109 (or some other external device), and the ICD 106.

In FIG. 1A, the two LPs 102 and 104 are shown as being implanted endocardially, i.e., within respective cardiac chambers. In other words, in FIG. 1A each of the LPs 102 and 104 is shown as being implanted in a respective cardiac chamber, i.e., the LP 102 is shown as being implanted in the RA chamber, and the LP 104 is shown as being implanted in the RV chamber. Alternatively, one or both of the LPs 102 and 104 can be implanted epicardially (on the external heart surface) by affixing to the exterior surface of the heart. For example, it would also be possible for the LP 102 to be affixed to an exterior surface of the RA chamber, in which case the LP 102 can be said to be implanted on (rather than in) the RA chamber. Similarly, it would also be possible for the LP 104 to be affixed to an exterior of the RV chamber, in which case the LP 104 can be said to be implanted on (rather than in) the RV chamber. More generally, an LP can either be implanted in or on the cardiac chamber that the LP is being used to pace. It is noted that the terms "implanted in," "implanted within," "located in," and "located within" are used interchangeably herein when referring to where a particular LP is implanted. Further, it is noted that the terms "located on" and "implanted on" are used interchangeably herein when referring to where a particular LP is implanted. The cardiac chamber within or on which a particular LP is implanted can be referred to as a "local chamber", while another chamber (within or on which the particular LP is not implanted) can be referred to as a "remote chamber".

In accordance with certain embodiments, methods are provided for coordinating operation between LPs located in or on different cardiac chambers of the heart. Some such methods can configure a local LP to receive communications from a remote LP through conductive communication. Some such methods rely on a local LP sensing a far-field signal and/or a sensor signal to itself monitor cardiac activity associated with a remote cardiac chamber.

Figure 1B:
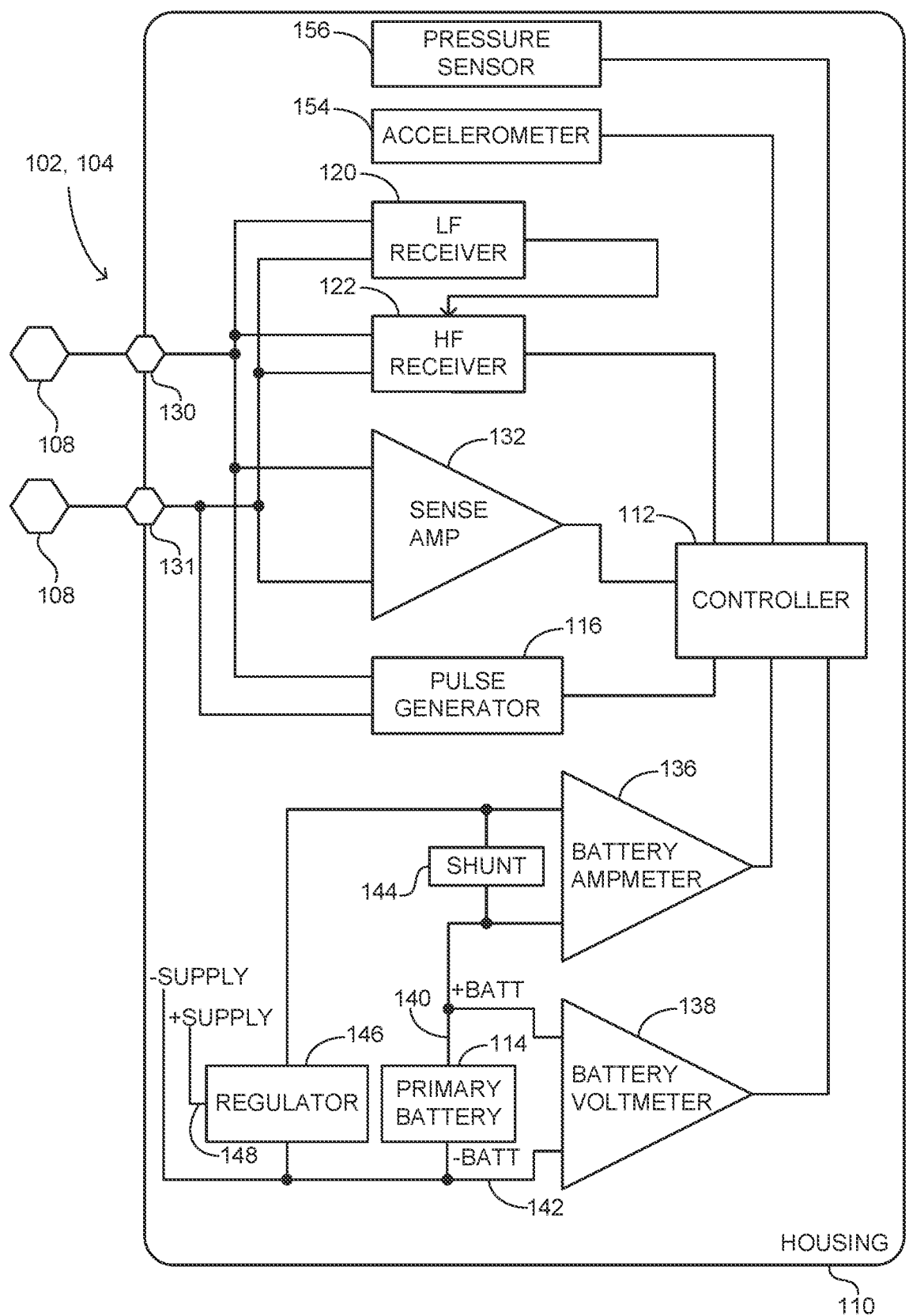
FIG. 1B is a block diagram of an exemplary leadless pacemaker (LP) in accordance with certain embodiments herein.

Referring to FIG. 1B, a block diagram shows exemplary electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, the programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed. Alternatively, the external programmer 109 may wait for a directed communication message transmitted to the external programmer 109 from LP 102 or 104 that indicates to the external programmer 109 that that the LP is ready to trade communication signals 113 with the external programmer 109. An LP 102, 104 can also communicate with other types of external devices besides the external programmer 109, such as, but not limited to, an external monitor.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 µA. The same LP 102, 104 may implement an event message utilizing event signaling parameters for amplitude, pulse-width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body. As will be described in additional detail below, with reference to FIGS. 9A and 9B, in certain embodiments an individual LP includes two hermetic housings, one of which includes electronic circuitry, and the other of which includes a battery.

Referring to FIG. 1B, the LP 102 (or 104) is shown as including an accelerometer 154 which can be hermetically contained within the housing 110. The accelerometer 154 can be any one of various different types of well known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and U.S. Pat. No. 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for the accelerometer 154 to be a beam-type of accelerometer, an example of which is described in U.S. Pat. No. 6,252,335 (Nilsson et al.), which is incorporated herein by reference.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of g≈9.81 m/s^2.

Where an LP (e.g., LP 102 or 104) includes an accelerometer within a housing of the LP or attached thereto, the accelerometer can be used to measure the acceleration of the LP along one or more axes, which measurement(s) can be used to determine the orientation of the LP. Accordingly, because the output(s) of the accelerometer can be used to determine the orientation of the LP, it can be said that the output(s) of the accelerometer (e.g., 154) are indicative of an orientation of the LP (e.g., LP 102 or 104). More specifically, in accordance with certain embodiments, the controller 112 of an LP 102 (or 104) receives one or more outputs output(s) of the accelerometer 154, which is/are indicative of an orientation of the LP 102 (or 104). In such embodiments, the controller 112 can determine, based on the output(s) received from the accelerometer 154, an actual orientation of the LP 102 (or 104). Each output of the accelerometer 154 can comprise a respective signal.

One or more signals produced and output by the accelerometer 154 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the accelerometer 154 can be analog signals, which can be analyzed in the analog domain, or can be converted to digital signals (by an analog-to-digital converter) and analyzed in the digital domain. Alternatively, the signals output by the accelerometer 154 can already be in the digital domain.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology. In accordance with certain embodiments of the present technology, described in additional detail below, a sensor signal produced by the accelerometer 154 of an LP implanted in or on a cardiac chamber can be used to detect mechanical cardiac activity associated with another cardiac chamber.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

In FIG. 1B, all of the components shown within the housing 110, besides the battery 114, can be referred generally as electrical circuitry or electronics of the LP 102, 104. In FIG. 1B the battery 114 and the electronics are shown as being within the same housing 110. In certain embodiments of the present technology, described below with reference to FIGS. 9A and 9B, the battery 114 and the electronics are included within separate respective electrically conductive housings (e.g., 912 and 922 in FIG. 9A) that are electrically isolated from one another.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102, 104 and/or the ICD 106 and transmit data including designated codes for events detected or created by an individual LP. Individual LPs can be configured to issue a unique code corresponding to an event type and a location of the sending pacemaker. While the LP 102, 104 shown in FIG. 1B is shown as including only two electrodes 108, in alternative embodiments discussed below, an LP can include more than two electrodes.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIG. 1A, the cardiac pacing system 100 may comprise an implantable cardioverter-defibrillator (ICD) 106 in addition to LPs 102, 104 configured for implantation in electrical contact with a cardiac chamber and for performing cardiac rhythm management functions in combination with the implantable ICD 106. The implantable ICD 106 and the one or more LPs 102, 104 can be configured for leadless intercommunication by information conduction through body tissue and/or wireless transmission between transmitters and receivers in accordance with the discussed herein.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, or one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACap-Confirm, sensing sensitivities, etc.).

Also shown in FIG. 1B, the primary battery 114 has positive pole 140 and negative pole 142. Current from the positive pole 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102, 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102, 104 can be used to sense an intracardiac electrocardiogram (IEGM) from which atrial and/or ventricular activity can be detected, e.g., by detecting R waves and/or P waves. Accordingly, the sensed IEGM can be used by an LP to time its delivery of pacing pulses. Where an IEGM sensed by an LP is indicative of electrical cardiac activity associated with the same cardiac chamber within or on which an LP is implanted, the IEGM can be referred to as a near-field signal. Where an IEGM sensed by an LP is indicative of electrical cardiac activity associate with another cardiac chamber of the heart (other than the cardiac chamber within or on which the LP is implanted), the IEGM can be referred to as a far-field signal. An IEGM can also be used by an LP 102, 104 to time when i2i communication pulses should be generated and transmitted, since the orientation of the LPs 102, 104 relative to one another can change throughout each cardiac cycle.

Figure 2:
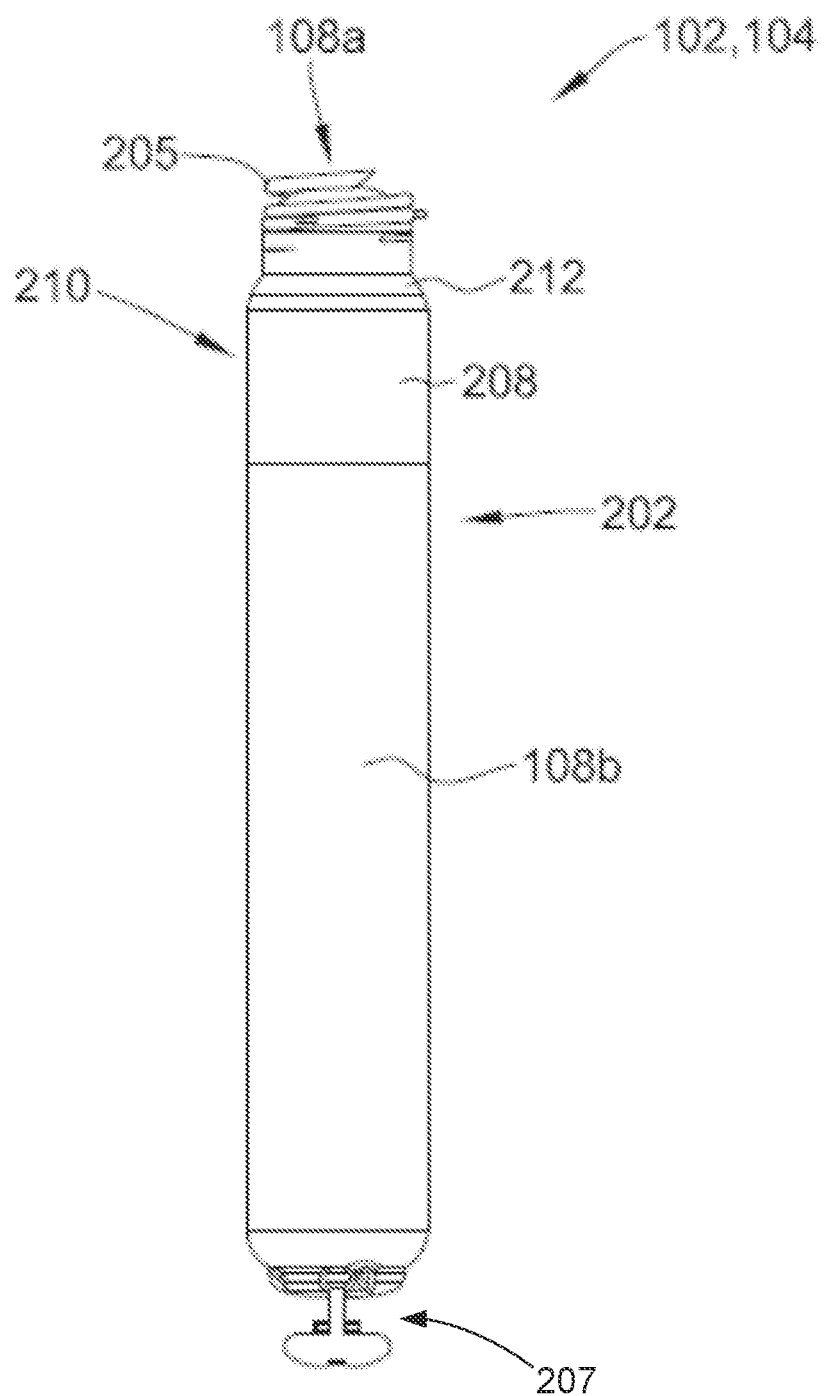
FIG. 2 illustrates an LP in accordance with certain embodiments herein.

FIG. 2 shows an LP 102, 104. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation. The electrode 108a is an example of a tip electrode, and the electrode 108b is an example or a ring electrode. The electrodes 108a and 108b can be referred to collectively as the electrodes 108, or individually as the electrode 108. While the LP 102, 104 shown in FIG. 2 is shown as including only two electrodes 108, in alternative embodiments discussed below, an LP can include more than two electrodes. The LP 102, 104 shown in FIG. 2 is also shown as including a retrieval feature 207, which can include a "button" or circular grasping feature that is configured to dock within a docking cap or a retrieval catheter that can be used to remove the LP 102, 104 when it needs to be removed and/or replaced. Alternative form factors for the retrieval feature are also possible.

Where an LP includes more than two electrodes, a first subset of the electrodes can be used for delivering pacing pulses, a second subset of the electrodes can be used for sensing a near-field signal, a third subset of the electrodes can be used for sensing a far-field signal, and a fourth subset of the electrodes can be used for transmitting and receiving i2i messages. One or more of the first, second, third, and forth subsets of electrodes can be the same, or they can all differ from one another. As used herein, the term near-field signal refers to a signal that originates in a local chamber (i.e., the same chamber) within which or on which corresponding sense electrodes (and the LP including the sense electrodes) are located. Conversely, the term far-field signal refers to a signal that originates in a chamber other than the local chamber within which or on which corresponding sense electrodes (and the LP including the sense electrodes) are located.

The housing 202 can also include an electronics compartment 210 within the housing that contains the electronic components necessary for operation of the pacemaker, including, e.g., a pulse generator, receiver, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate electrodes 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208. As noted above, and described in additional detail below, an LP can include more than two electrodes, and may use different combinations of the electrodes for sensing a near-field signal, sensing a far-field signal, delivering pacing pulses, and sending and receiving i2i messages. When the electrode 108a is used as a pace electrode it can also be referred to as the cathode.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode (also referred to as the anode) for sensing and pacing. The fixation mechanism may be coated partially or in full for electrical insulation, and a steroid-eluting matrix may be included on or near the device to minimize fibrotic reaction, as is known in conventional pacing electrode-leads.

Implant-to-Implant (i2i) Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within (or alternatively on) first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 3:
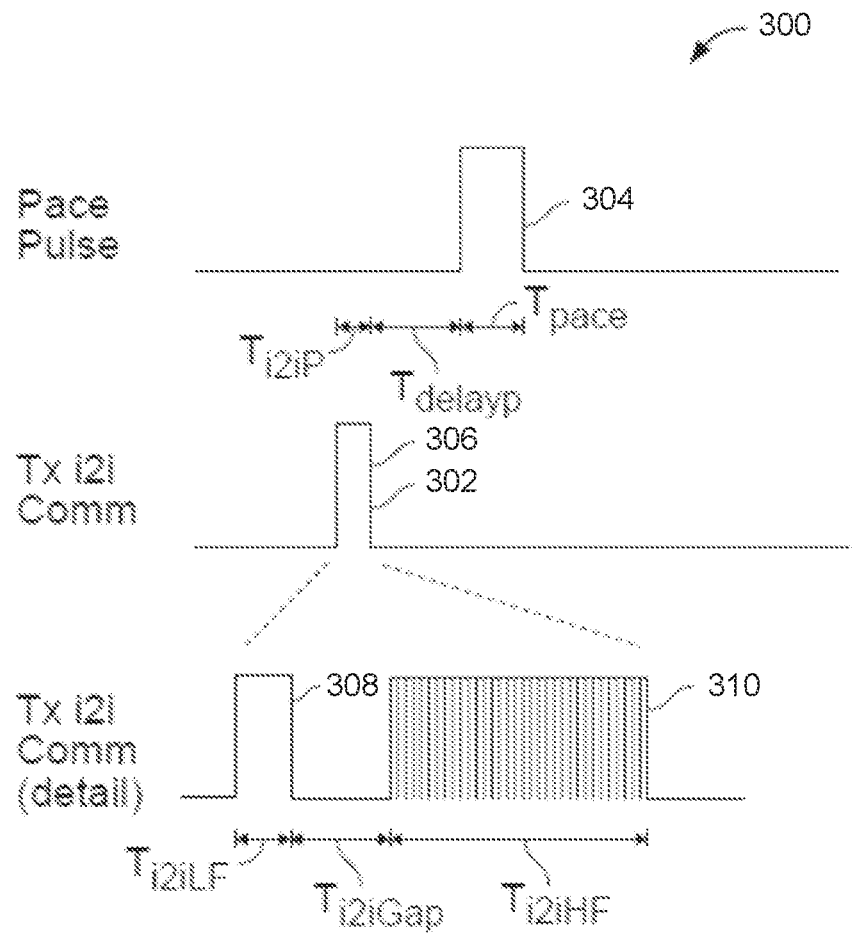
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from LP 102 to LP 104. As shown in FIG. 3, in this embodiment, an i2i transmission 302 is sent prior to delivery of a pace pulse 304 by the transmitting LP (e.g., LP 102). This enables the receiving LP (e.g., LP 104) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period $T_{i2iLF}$, and high frequency pulse train 310 lasts for a period $T_{i2iHF}$. The end of low frequency pulse 308 and the beginning of high frequency pulse train 310 are separated by a gap period, $T_{i2iGap}$.

As shown in FIG. 3, the i2i transmission 302 lasts for a period Ti2iP, and pace pulse 304 lasts for a period Tpace. The end of i2i transmission 302 and the beginning of pace pulse 304 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means+/−10% of a specified value.

Figure 4:
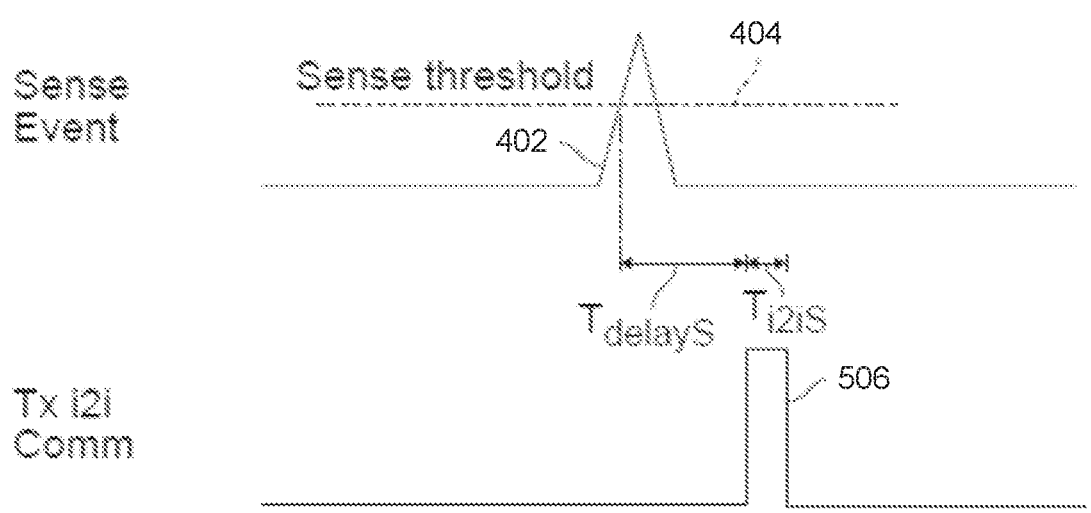
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from LP 102 to LP 104. As shown in FIG. 4, in this embodiment, the transmitting LP (e.g., LP 102) detects the sensed event when a sensed intrinsic activation 402 crosses a sense threshold

404. A predetermined delay period, $T_{delayS}$, after the detection, the transmitting LP transmits an i2i transmission 406 that lasts a predetermined period $T_{i2iS}$. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 406, the envelope of i2i transmission 406 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 2 represents exemplary event markers sent from the aLP to the vLP, while Table 3 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 2

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 2, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 3

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 3, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In the event that LP to LP (i2i) communication is lost (prolonged or transient), the system 100 may automatically revert to safe ventricular-based pace/sense functionalities as the vLP device is running all of the necessary algorithms to independently achieve these functionalities. For example, if the vLP loses i2i communication it may revert from the VDD mode to a WI mode or a VDI mode, and if the aLP loses i2i communication it may revert from ADD mode to an OAO mode or an AAI mode. Thereafter, once i2i communication is restored, the system 100 can automatically resume dual-chamber functionalities.

As noted above, when using a pair of LPs (e.g., 102, 104) to perform pacing and/or sensing operations in the RA and RV, one of the challenges is that i2i communication may be relied upon to maintain appropriate synchrony between the RV and the RA.

As also noted above, a transmitter (e.g., 118) of an LP 102, 104 may be configured to transmit event messages in a manner that does not inadvertently capture the heart in the chamber where LP 102, 104 is located, such as when the associated chamber is not in a refractory state. In addition, an LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104. The amplitude of a detected (i.e., sensed) measurement pulse can be referred to as the sensed amplitude.

As noted above, it has been observed that i2i communication can be adversely affected by the orientation of the LPs relative to one another. Both computer simulations and animal testing have showed that sensed i2i amplitude varied widely with different orientation angles. For example, where a first LP (e.g., 102) transmits a pulse having a pulse amplitude of 2.5V to a second LP (e.g., 104), the sensed amplitude of the pulse received by the second LP (e.g., 104) could vary from about 2 mV to less than 0.5 mV, depending upon the orientation between the first and second LPs (e.g., 102 and 104). For example, where the LP 102 is implanted in or on the RA chamber, and the LP 104 is implanted in or on the RV chamber, e.g., as shown in FIG. 1A, the orientation of the LPs 102 and 104 relative to one another can change over the course of each cardiac cycle. Additionally, the orientation of the LPs 102 and 104 relative to one another can be affected by the posture of the patient. Accordingly, since the sensed amplitude of an i2i pulse received by one LP (e.g., 104) from the other LP (e.g., 102) can significantly vary based on the orientation of the LPs relative to one another, the sense i2i amplitude can significantly vary depending upon the timing of when an i2i pulse is transmitted during a cardiac cycle, as well as the posture of the patient when the pulse is transmitted.

Assume, for example, that an LP 102, 104 has a 0.5 mV i2i sense threshold, meaning that a sensed pulse must have an amplitude of at least 0.5 mV in order to be detected as a communication pulse by the receiving LP. In other words, if sensed amplitudes of received communication pulses are below the sense threshold, the receiving LP will fail to receive the information encoded therein and may fail to respond accordingly, which is undesirable.

Figure 5:
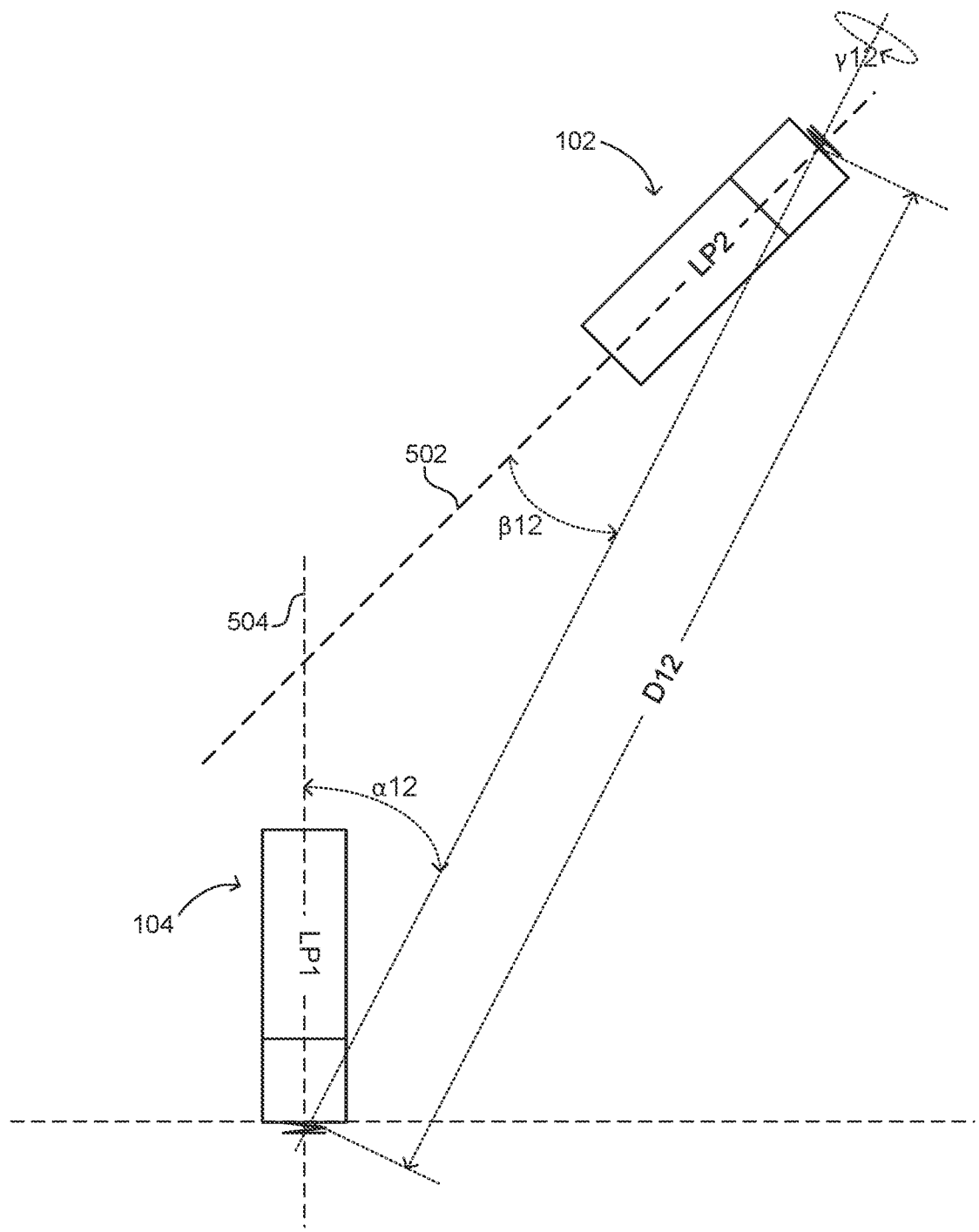
FIG. 5 is a diagram that is used to show how the orientation of two different LPs can be quantified in accordance with certain embodiments of the present technology.

FIG. 5 is a diagram that is used to show how the orientation of two different LPs (e.g., 102, 104), labeled LP2 and LP1 in FIG. 5, can be quantified. Referring to FIG. 5, the LP2 (e.g., 102) is shown as having an axis 502, and the LP1 (e.g., 104) is shown as having an axis 504. The line D12 represents the distance between the LP1 and the LP2. In FIG. 5, the angle $\alpha 12$ is the angle between the axis 504 of the LP1 and the line D12; the angle $\beta 12$ is the angle between the axis 502 of the LP2 and the line D12; and the angle $\gamma 12$ is angle between the plane defined by the angle $\alpha 12$ and the plane defined by the angle $\beta 12$.

Table 3, below, provides the results of simulations that show how sensed amplitudes are affected by the orientation of LP1 and LP2 relative to one another, where the LP2 is assumed to be implanted in the RA chamber, the LP1 is assumed to be implanted in the RV chamber, and the distance D12 is assumed to be fixed at 124 millimeters (mm).

TABLE 4

| Distance D12 | Angle $\alpha 12$ | Angle $\beta 12$ | RA → RV | RA ← RV |
|---|---|---|---|---|
| 124 mm | 20° | 12° | 2.5 V → 2.13 mV | 2.11 mV ← 2.5 V |
| 124 mm | 20° | 32° | 2.5 V → 1.82 mV | N/A |
| 124 mm | 20° | 52° | 2.5 V → 1.32 mV | N/A |
| 124 mm | 20° | 72° | 2.5 V → 0.745 mV | N/A |
| 124 mm | 20° | 82° | 2.5 V → 0.470 mV | 0.460 mV ← 2.5 V |
| 124 mm | 20° | 92° | 2.5 V → 0.198 mV | 0.198 mV ← 2.5 V |
| 124 mm | 10° | 82° | 2.5 V → 0.6627 mV | N/A |
| 124 mm | 40° | 82° | 2.5 V → −0.1135 mV | N/A |

The first row of Table 4 shows that when the angle $\beta 12$ (i.e., the angle between the axis 502 of the LP2 and the line D12) is 12 degrees, in response to the LP2 transmitting a communication pulse having an amplitude of 2.5V, the sense amplitude of the communication pulse received by the LP1 will be 2.13 mV, which is well above a 0.5 mV sense threshold. By contrast, the sixth row of Table 4 shows that when the angle $\beta 12$ is 92 degrees, in response to the LP2 transmitting a communication pulse having an amplitude of 2.5V, the sense amplitude of the communication pulse received by the LP1 will be only 0.198 mV, which is well below the 0.5 mV sense threshold. Looking at the right most column and the first row of Table 4 shows that when the angle $\beta 12$ is 12 degrees, in response to the LP1 transmitting a communication pulse having an amplitude of 2.5V, the sense amplitude of the communication pulse received by the LP2 will be 2.11 mV, which is well above a 0.5 mV sense threshold; and when the angle $\beta 12$ is 92 degrees, in response to the LP1 transmitting a communication pulse having an amplitude of 2.5V, the sense amplitude of the communication pulse received by the LP2 will be only 0.198 mV, which is well below the 0.5 mV sense threshold.

With larger heart sizes, the sensed amplitudes decrease. More specifically, a larger heart can cause the distance D12 between the LP1 and the LP2 to increase, with the results summarized in Table 5, below.

TABLE 5

| Distance D12 | Angle α12 | Angle β12 | RA → RV | RA ← RV |
|---|---|---|---|---|
| 150 mm | 20° | 12° | 2.5 V → 0.96 mV | N/A |
| 150 mm | 20° | 32° | 2.5 V → 0.76 mV | N/A |
| 150 mm | 20° | 52° | 2.5 V → 0.51 mV | N/A |
| 150 mm | 20° | 72° | 2.5 V → 0.25 mV | N/A |
| 150 mm | 20° | 82° | 2.5 V → 0.12 mV | N/A |
| 150 mm | 20° | 92° | 2.5 V → 0.005 mV | N/A |
| 150 mm | 20° | 52° | 2.5 V → 0.51 mV | N/A |
| 150 mm | 10° | 52° | 2.5 V → 0.59 mV | N/A |
| 150 mm | 40° | 52° | 2.5 V → 0.27 mV | N/A |

The results summarized in Table 5 mimic a worst case where the heart size is at the upper bounds (D12~150 mm). As can be appreciated from a comparison between Table 5 and Table 4, the sensed amplitudes decreased as D12 was increased from 124 mm to 150 mm, so that in Table 5 when the angle β12 is greater than 52 degree, the sensed amplitude is lower than the 0.5 mV sense threshold. Accordingly, it can be appreciated that i2i communications between LPs implanted in larger hearts are even more adversely affected than smaller hearts by the relative orientation of the LPs.

When performing i2i communication, the one or more pulses that are transmitted from one LP to another LP can be referred more generally as the i2i signal. Due to the nature of electrode potential distribution, bipolar sensing of the i2i signal (by the LP that is receiving/sensing the i2i signal) is minimal along iso-potential lines and maximum along lines orthogonal to the iso-potential lines. In other words, when the respective axes (e.g., 502 and 504 in FIG. 5) of the two LPs (communicating with one another) are aligned with one another the sensed i2i signal is near its maximum, and when the respective axes (e.g., 502 and 504 in FIG. 5) of the two LPs are orthogonal to one another the sensed i2i signal is near its minimum.

For the purpose of this discussion, when the LPs are oriented relative to another such that (for a give transmitted communication pulse amplitude) the sense amplitude of the communication pulse received by an LP will be below the sense threshold (e.g., 0.5 mV), the LPs can be said to be within a "deaf zone". This is because under such circumstances the LPs cannot successfully communicate or "hear" one another even though they are attempting to communicate or "talk" with one another.

Use of Far-Field and/or Sensor Signals to Supplement or Replace i2i Messaging

In accordance with certain embodiments of the present technology, one or more accelerometers of an LP can be used to determine when the LP is likely in a deaf zone, and during such periods the LP can rely on far-field sensing to time delivery of pacing within the chamber in which the LP is implanted. For example, the aLP can sense a far-field signal from which electrical cardiac activity associated with the RV chamber can be detected, and the aLP can perform ADD pacing by timing delivery of atrial pulses based on the timing of cardiac activity associated with the RV chamber as detected from the far-field signal. For another example, the vLP can sense a far-field signal from which electrical cardiac activity associated with the RA chamber can be detected, and the vLP can perform VDD pacing by timing delivery of ventricular pulses based on the timing of cardiac activity associated with the RA chamber as detected from the far-field signal. When an aLP implanted in the RA chamber times delivery of atrial pacing pulses based on the timing of RV cardiac activity as detected from a far-field signal sensed by the aLP, it can be said that the aLP times its delivery of atrial pacing pulses based on timing of RV cardiac activity detected by the aLP itself. Similarly, when an vLP implanted in the RV chamber times delivery of ventricular pacing pulses based on the timing of RA cardiac activity as detected from a far-field signal sensed by the vLP, it can be said that the vLP times its delivery of ventricular pacing pulses based on timing of RA cardiac activity as detected by the vLP itself.

Depending upon the specific implementation, an aLP can primarily or by default time delivery of RA pacing pulses based on the timing of cardiac activity associated with the RV chamber as determined based on i2i messages received by the aLP from a vLP, and the aLP can, as a backup, time delivery of RA pacing pulses based on the timing of cardiac activity associated with the RV chamber that the aLP detected itself from a far-field signal that the aLP sensed. Similarly, a vLP can primarily or by default time delivery of RV pacing pulses based on the timing of cardiac activity associated with the RA chamber as determined based on i2i messages received by the vLP from an aLP, and the vLP can, as a backup, time delivery of RV pacing pulses based on the timing of cardiac activity associated with the RA chamber that the vLP detected itself from a far-field signal that the vLP sensed.

Alternatively, an aLP can primarily or by default time delivery of RA pacing pulses based on the timing of cardiac activity associated with the RV chamber as determined based on a far-field signal that the aLP sensed itself, and the aLP can, as a backup, time delivery of RA pacing pulses based on the timing of cardiac activity associated with the RV chamber as determined based on i2i messages received by the aLP from a vLP. Similarly, a vLP can primarily or by default time delivery of RV pacing pulses based on the timing of cardiac activity associated with the RA chamber as determined based on a far-field signal that the vLP sensed itself, and the vLP can, as a backup, time delivery of RV pacing pulses based on the timing of cardiac activity associated with the RA chamber as determined based on i2i messages received by the vLP from an aLP.

In accordance with certain embodiments of the present technology, instead of (or in addition to) an LP detecting electrical cardiac activity associated with another chamber based on a far-field signal sensed by the LP itself, the LP can use a sensor (e.g., an accelerometer or pressure sensor) to produce a sensor signal from which mechanical cardiac activity associated with another chamber of the heart may be detected. For example, the aLP can use an accelerometer or pressure sensor to produce a sensor signal from which heart sounds associated with the RV chamber can be detected, and the aLP can perform ADD pacing by timing delivery of atrial pulses based on the timing of cardiac activity associated with the RV chamber as detected from the sensor signal. For another example, the vLP can use an accelerometer or pressure sensor to produce a sensor signal from which mechanical cardiac activity associated with the RA chamber can be detected, and the vLP can perform VDD pacing by timing delivery of ventricular pulses based on the timing of cardiac activity associated with the RA chamber as detected from the sensor signal.

Where the vLP performs VDD pacing, it performs ventricular pacing, atrial and ventricular (i.e., dual) sensing, dual (i.e., triggered and inhibited) response to a sensed event. VDD may be used, e.g., for AV nodal dysfunction but intact and appropriate sinus node behavior. The ventricular sensing can be based on a near-field signal that the vLP senses itself using a pair of its electrodes. Similarly, if the vLP performs VVI or VDI pacing, it can perform ventricular sensing based on a near-field signal that the vLP senses itself using a pair of its electrodes. Atrial sensing can be based on a far-field signal that the vLP senses itself using a pair of its electrodes, based on a sensor signal that vLP senses itself (e.g., using an accelerometer or pressure sensor of the vLP), and/or based on i2i messages that the vLP receives from the aLP.

Where the aLP performed ADD pacing, it performs atrial pacing, atrial and ventricular (i.e., dual) sensing, dual (i.e., triggered and inhibited) response to a sensed event. The atrial sensing can be based on a near-field signal that the aLP senses itself using a pair of its electrodes. Similarly, if the aLP performs AAI or ADI pacing, it can perform atrial sensing based on a near-field signal that the aLP senses itself using a pair of its electrodes. Ventricular sensing can be based on a far-field signal that the aLP senses itself using a pair of its electrodes, based on a sensor signal that aLP senses itself (e.g., using an accelerometer or pressure sensor of the aLP), and/or based on i2i messages that the aLP receives from the vLP.

Figure 6:
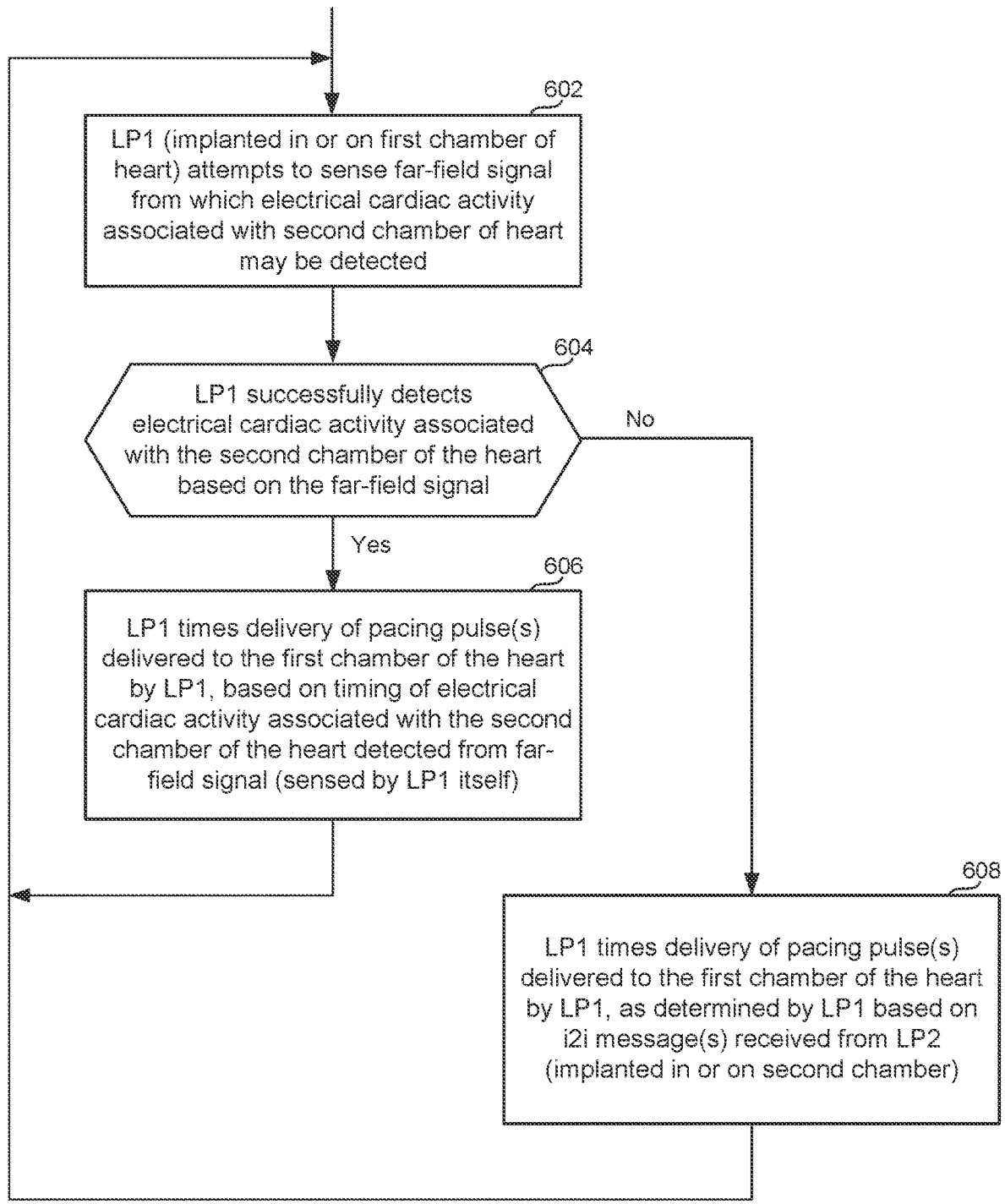
FIG. 6 is a high level flow diagram that is used to describe embodiments of the present technology where an LP implanted in or on a chamber of a heart preferably or by default attempts to time its pacing pulses (relative to activity of a remote chamber) based on electrical cardiac activity associated with another chamber of the heart as determined from a sensed far-field signal, and as a backup, uses i2i messages received from an LP implanted in or on the other chamber when a far-field signal is not successfully detected.

The high level flow diagram of FIG. 6 will now be used to describe certain embodiments of the present technology for use with an implantable system including a first leadless pacemaker (LP1) implanted in or on a first chamber of a heart and a second leadless pacemaker (LP2) implanted in or on a second chamber of the heart, wherein the LP1 includes a plurality of electrodes at least two of which can be used by the LP1 to transmit and receive implant-to-implant (i2i) messages to and from the LP2. More specifically, the high level flow diagram of FIG. 6 will be used to describe a method for use by the LP1 that is implanted in or on the first chamber of the heart. For the embodiments described with reference to FIG. 6, it is assumed that the LP1 preferably or by default attempts to time its pacing pulses (relative to activity of a remote chamber) based on a sensed far-field signal, and that i2i communication is used as a backup when the electrical cardiac activity associated with the second chamber of the heart is not successfully detected based on the far-field signal.

Referring to FIG. 6, at step 602 the LP1 (implanted in or on the first chamber of the heart) attempts to sense a far-field signal from which electrical cardiac activity associated with the second chamber of the heart may be detected. At step 604 there is a determination of whether the LP1 successfully detects electrical cardiac activity associated with the second chamber of the heart based on the far-field signal. There are various different ways that the determination at step 604 can be performed, depending on the specific implementation, as well as based on where the LP1 and LP2 are implanted. For example, if the first chamber of the heart (within or on which the LP1 is implanted) is the RV chamber, and the second chamber of the heart (for which cardiac activity is trying to be detected from far-field signal sensed by the LP1) is the RA chamber, then step 604 can be performed by determining whether indicators of RA chamber contractions (e.g., A or P waves) are successfully detected from the sensed far-field signal, and/or whether the SNR of the sensed far-field signal exceeds a specified threshold. For another example, if the first chamber of the heart (within which the LP1 is implanted) is the RA chamber, and the second chamber of the heart (for which cardiac activity is trying to be detected from far-field signal sensed by the LP1) is the RV chamber, then step 604 can be performed by determining whether indicators of RV chamber contractions (e.g., V or R waves) are successfully detected from the sensed far-field signal, and/or whether the SNR of the sensed far-field signal exceeds a specified threshold. These are just a few examples of how step 604 can be performed, which are not intended to be all encompassing.

If the answer to the determination is Yes, then flow goes to step 606, as shown in FIG. 6. At step 606 the LP1 times delivery of one or more pacing pulses to the first chamber of the heart (within or on which the LP1 is implanted) based on timing of electrical cardiac activity associated with the second chamber of the heart as detected from the far-field signal that the LP1 sensed itself. For example, if the first chamber of the heart (within or on which the LP1 is implanted) is the RV chamber, and the second chamber of the heart (for which cardiac activity is being detected from far-field signal sensed by the LP1) is the RA chamber, then step 606 can involve the LP1 timing delivery of one or more pacing pulses to the RV chamber based on the timing of A or P waves detected from the far-field signal that the LP1 sensed (and based on a programmed AV delay). For another example, if the first chamber of the heart (within or on which the LP1 is implanted) is the RA chamber, and the second chamber of the heart (for which cardiac activity is being detected from far-field signal sensed by the LP1) is the RV chamber, then step 606 can involve the LP1 timing delivery of one or more pacing pulses to the RA chamber based on the timing of V or R waves detected from the far-field signal that the LP1 sensed (and based on a programmed VA interval). These are just a few examples of how step 606 can be performed, which are not intended to be all encompassing.

If the answer to the determination is No, then flow goes to step 608, as shown in FIG. 6. At step 608 the LP1 times delivery of one or more pacing pulses delivered to the first chamber of the heart (within or on which the LP1 is implanted) based on timing of cardiac activity associated with the second chamber of the heart as determined by the LP1 based on i2i messages that the LP1 receives from the LP2 (implanted within or on the second chamber of the heart). The LP2 can send such i2i messages to the LP1 once per heartbeat, or the LP2 can send such i2i messages to the LP1 in response to a request from the LP1. Other variations are also possible.

Figure 7:
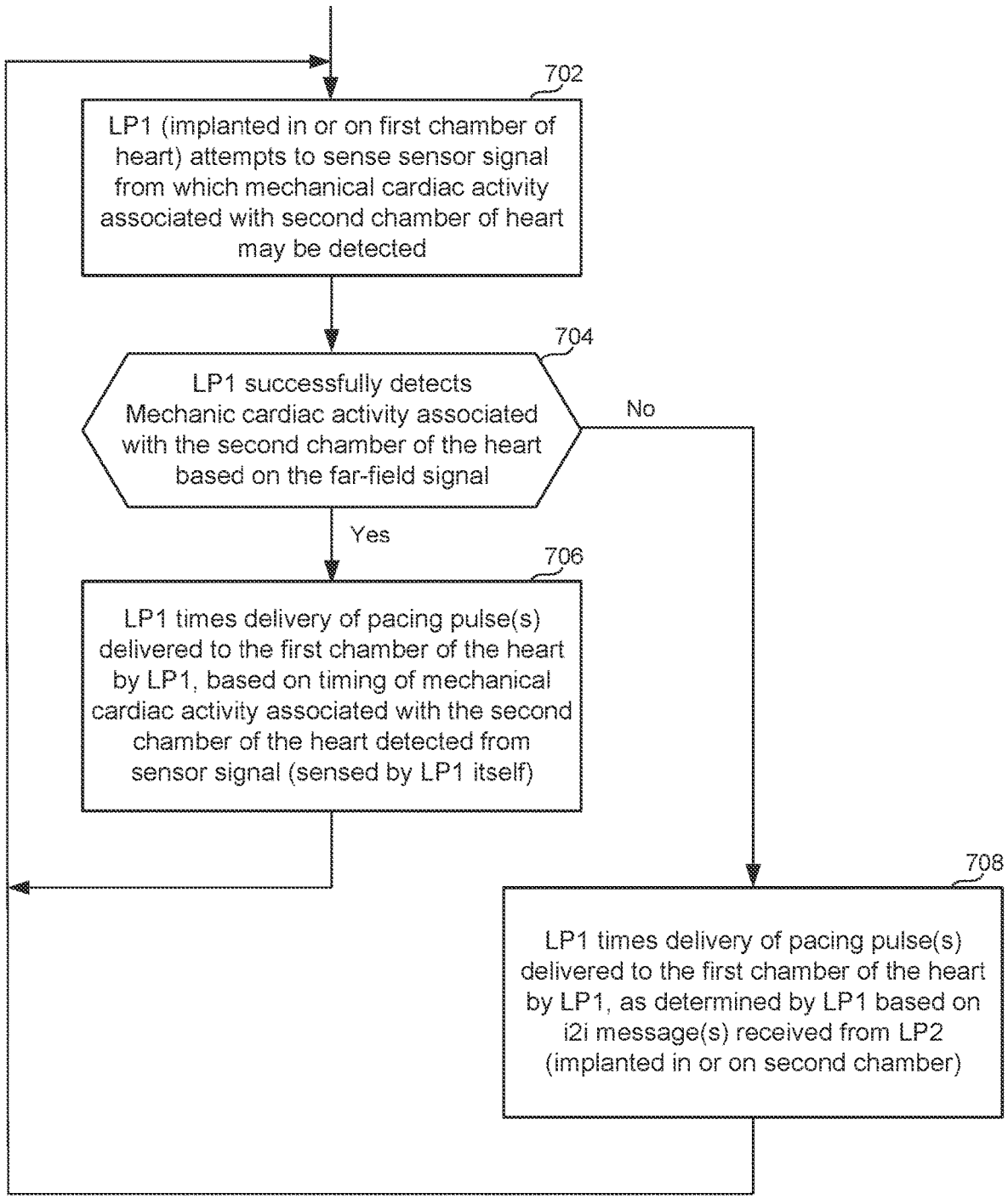
FIG. 7 is a high level flow diagram that is used to describe embodiments of the present technology where an LP implanted in or on a chamber of a heart preferably or by default attempts to time its pacing pulses (relative to activity of a remote chamber) based on mechanical cardiac activity associated with another chamber of the heart as determined from a sensor signal, and as a backup, uses i2i messages received from an LP implanted in or on the other chamber of the heart when a far-field signal is not successfully detected.

As can be appreciated from steps 702, 704, 706 and 708 shown in the high level flow diagram of FIG. 7, instead of (or in addition to) the LP1 (implanted in or on the first chamber of the heart) attempting to sense a far-field signal from which electrical cardiac activity associated with the second chamber of the heart may be detected, the LP1 can use a sensor of the LP1 to sense a sensor signal from which mechanical cardiac activity associated with the second chamber of the heart may be detected. In such an embodiment, the LP1 can use the sensor signal (instead of, or in addition to the far-field signal) to time delivery of pacing to the first chamber of the heart (within or on which the LP1 is implanted). For example, the sensor can be an accelerometer (e.g., 154) or a pressure sensor (e.g., 156 in FIG. 1B) from which heart sounds and/or other indicators of mechanical cardiac activity may be detected. Heart sounds are the noises generated by the beating heart and the resultant flow of blood, and are typically referred to as S1, S2, S3 and S4. Depending upon which heart sound is being detected, the LP1 can appropriately time its pacing therapy.

The S1 heart sound, which is typically the loudest and most detectable of the heart sounds, is caused by the sudden block of reverse blood flow due to closure of the atrioventricular valves (mitral and tricuspid) at the beginning of ventricular contraction. Isovolumic relaxation (IR) occurs during ventricular diastole and is demarcated approximately by closure of the aortic valve and the second heart sound (S2) and approximately by opening of the mitral valve and the third heart sound (S3), which is more prominent in children and those with abnormal ventricular function when compared to normal adults. The onset of isovolumic relaxation time commences with aortic valve closure, which can be identified by the aortic component (A2) of the second heart sound (S2). The third heart sound (S3) has been linked to flow between the left atrium and the left ventricle, more generally LV filling, and thought to be due to cardiohemic vibrations powered by rapid deceleration of transmitral blood flow. The fourth heart sound (S4) may be present in the late stage of diastole and associated with atrial contraction, or kick, where the final 20% of the atrial output is delivered to the ventricles.

Figure 8:
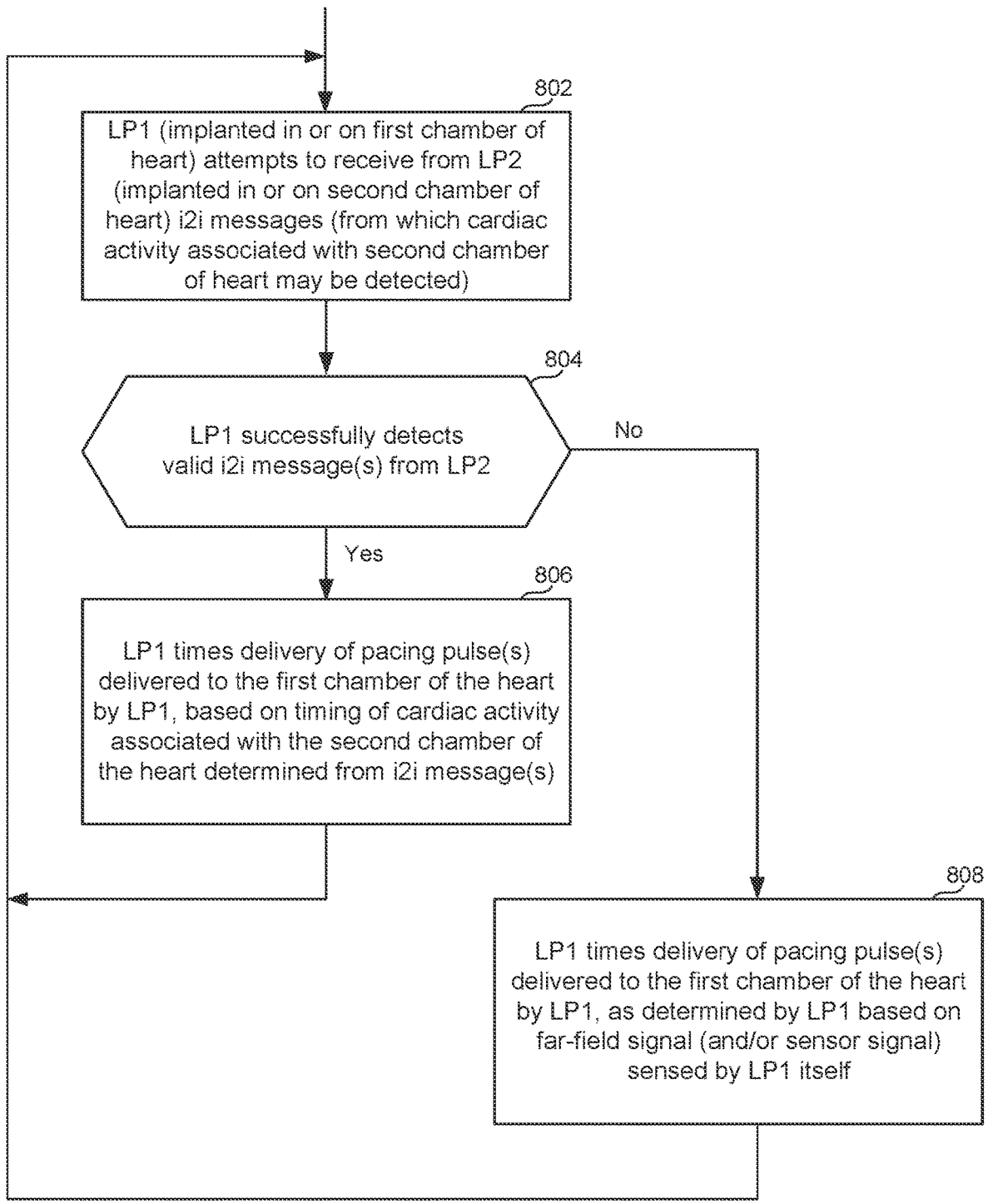
FIG. 8 is a high level flow diagram that is used to describe embodiments of the present technology where an LP implanted in or on a chamber of a heart preferably or by default uses i2i messages (received from an LP implanted in or on another chamber of the heart) to time its pacing, and as a backup, uses a far-field signal and/or sensor signal to time its pacing when valid i2i messages are not successfully received.

For the embodiments described with reference to FIG. 8, it is assumed that the LP1 preferably or by default attempts to time its pacing pulses (relative to activity of a remote chamber) based on i2i communication, and uses a sensed far-field signal (from which electrical cardiac activity may be detected) and/or a sensor signal (from which mechanical cardiac activity may be detected) as a backup when valid i2i messages are not detected from the LP2. Referring to FIG. 8, at step 802 the LP1 (implanted in or on a first chamber of heart) attempts to receive from the LP2 (implanted in or on a second chamber of heart) i2i messages from which cardiac activity associated with second chamber of heart may be detected.

At step 804 there is a determination of whether the LP1 has successfully detected valid i2i message(s) from the LP2. The term "i2i message", as used herein, can refer to an actual i2i sent message that is received and is capable of being decoded, an actual sent i2i message that is received but is too noisy to be decoded, an actual sent i2i message that is received but due to noise it is decoded mistakenly for a different i2i message, noise that is initially mistaken for being an actual i2i message but is sufficiently different than an actual i2i message so that it cannot be decoded, as well as noise that is received and is mistaken for being an actual i2i message and is decoded by the LP because the noise is sufficiently similar to an actual i2i message. The term "valid i2i message", as used herein, refers to an actual sent i2i message that is received and is capable of being decoded. In accordance with certain embodiments, the determination of whether an i2i message is valid or invalid can be performed by a processor or controller that performs error detection or correction.

If the answer to the determination at step 804 is Yes, then flow goes to step 806, as shown in FIG. 8. At step 806, the LP1 times delivery of one or more pacing pulses to the first chamber of the heart (within or on which the LP1 is implanted) based on cardiac activity associated with the second chamber of the heart determined from the received i2i message(s). For example, if the first chamber of the heart (within or on which the LP1 is implanted) is the RV chamber, and the second chamber of the heart (within or on which the LP2 is implanted) is the RA chamber, then step 806 can involve the LP1 timing delivery of one or more pacing pulses to the RV chamber based on the timing of atrial activity as determined from i2i messages received from the LP2 (and based on a programmed AV delay). For another example, if the first chamber of the heart (within or on which the LP1 is implanted) is the RA chamber, and the second chamber of the heart (within or on which the LP2 is implanted) is the RV chamber, then step 806 can involve the LP1 timing delivery of one or more pacing pulses to the RA chamber based on the timing of ventricular activity as determined from i2i messages received from the LP2 (and based on a programmed VA interval). These are just a few examples of how step 606 can be performed, which are not intended to be all encompassing. If the answer to the determination at step 804 is No, then flow goes to step 808, as shown in FIG. 8. Step 808 it similar to step 602 and/or step 702 described above, and thus, need not be described in detail again.

In still other embodiments, the LP1 (that is implanted within or on the first chamber of the heart) can test and compare use of a far-field signal, a sensor signal, and i2i messages, for use in timing delivery of one or more pacing pulses delivered to the first chamber of the heart by the LP1. Such testing can be performed every heartbeat, periodically, or in response to a triggering event, such as in response to signal quality of a selected signal falling below a specified level, or the like. Based on the results of the testing and comparing, the LP1 can select to use either the far-field signal, the sensor signal, or the i2i messages, for use in timing delivery of one or more pacing pulses delivered to the first chamber of the heart by the LP1. For example, the relative strength and/or robustness of a sensed far-field signal, i2i messages, and/or heart sounds can be used to select what type of signal local cardiac pacing should be based on. Strengths based on SNRs, discrimination capability, etc., can be used. It would also be possible to just test and compare two of the above three options to select one of the two tested and compared options for timing delivering of pacing pulse(s) to the local chamber of the heart by the LP1.

It would also be possible for the LP1 to select between timing delivering of its pacing pulses based on a far-field signal (and/or a sensor signal) and timing delivery of pacing pulses based on i2i messages, wherein the selecting is based on one or more accelerometer outputs indicative of the orientation of the LP1. For example, when the LP1 determines it's within or close to the deaf zone, it can choose to time delivery of pacing pulses based on a far-field signal (and/or a sensor signal), rather than relying on i2i messages. Conversely, when the LP1 is not within or close to the deaf zone, it can choose to time delivery of pacing pulses based on i2i message(s). Other variations are also possible.

In many of the embodiments described above, an implantable cardiac pacing system was described as including an LP implanted within or on the RA chamber and another LP implanted within or on the RV chamber. It would also be possible that one LP is implanted in or on the RV chamber and another LP is implanted in or on the LV chamber to allow for bi-ventricular pacing. It would also be possible for three LPs to be implanted, such that one is in the RV chamber, one is in the LV chamber, and another is in the RA chamber, to allow for CRT. In still other embodiments, it would also be possible to implant an LP in the LA chamber. Each of the LPs can itself detect cardiac activity associate with one or more other chamber by sensing a far-field signal from which electrical cardiac activity associated with one or more other chamber may be detected, and/or by using a sensor to produce a sensor signal from which mechanical cardiac activity associated with one or more other chamber may be detected. Each LP may also receive i2i messages from one or more other LP(s) implanted in or on one or more other cardiac chambers and can time their pacing pulses based on information learned from the i2i message. Accordingly, embodiments described herein, unless stated otherwise, should not be limited to LPs implanted in the RA and/or RV chambers.

In many of the embodiments discussed above, each LP was described as including two electrodes. However, an LP can include more than two electrodes. Exemplary LPs that include more than two electrodes are described below, e.g., with reference to FIGS. 9A and 9B. Were an LP includes more than two electrodes, the electrodes that the LP uses to sense a far-field signal can be the same as, or different than, the electrodes that the LP uses to transmit and receive i2i messages, as will be described in additional detail below. Each such i2i messages can be made up of one or more i2i pulses, exemplary details of which were described above.

Leadless Pacemaker (LP) Implementations

Figure 9A:
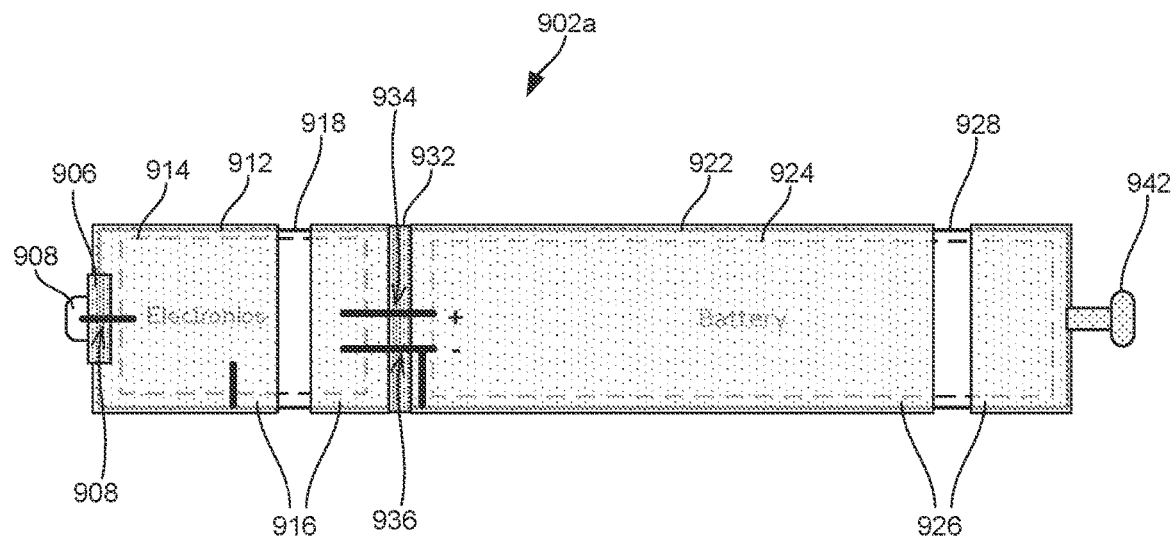
FIG. 9A is an illustration of an LP according to an embodiment of the present technology.
Figure 9B:
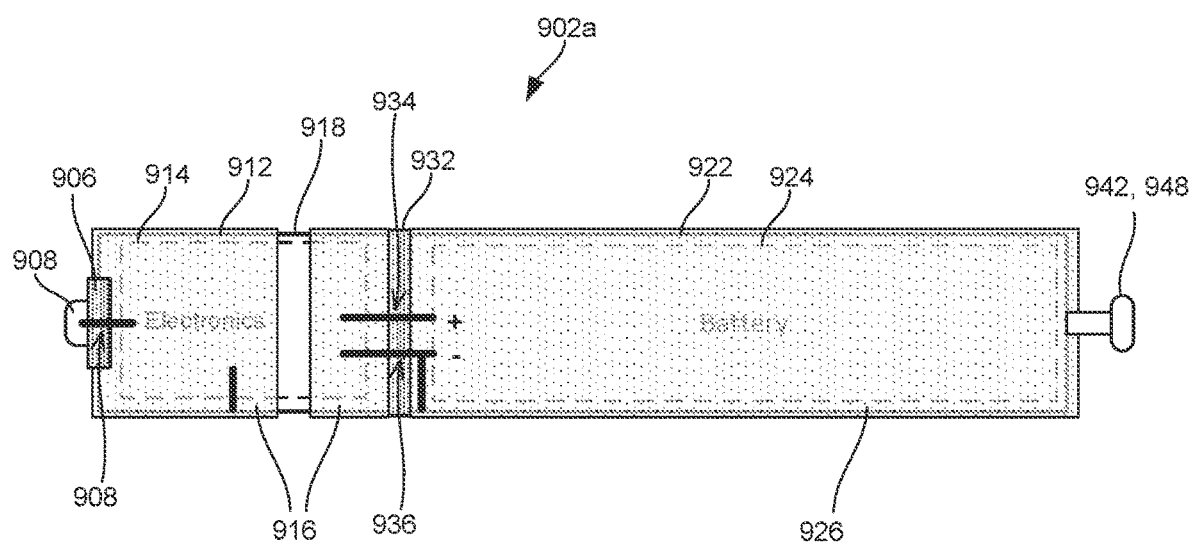
FIG. 9B is an illustration of an LP according to another embodiment of the present technology.

Certain embodiments of the present technology, described below with reference to FIGS. 9A and 9B, are related to specific implementations of an LP that enables the LP to effectively deliver pacing pulses to the cardiac chamber within or on which the LP is implanted, effectively sense near-field signals, as well as effectively sense far-field signals. A near-field signal can be used by the LP that senses the near-field signal to monitor electrical cardiac activity of the cardiac chamber within or on which the LP is implanted, which cardiac chamber can be referred to as the local chamber. A far-field signal can be used by the LP that senses the far-field signal to monitor electrical cardiac activity associated with another chamber of the heart (within or on which the LP that obtains the far-field signal is not implanted). Such other cardiac chamber of the heart (within or on which an LP is not implanted) can also be referred to herein as a remote chamber. The LP can also perform i2i communications.

Referring to FIG. 9A, an LP 902*a*, according to an embodiment of the present technology, is shown therein. The LP 902*a* is shown as including two separate housings 912 and 922, each of which is made of an electrically conductive material. The housings 912 and 922 can be made of the same type of electrically conductive material as one another, or of different types of electrically conductive materials than one another. The electrically conductive material of which the housing 912 and/or the housing 922 is made can be an electrically conductive biocompatible metal or alloy, such as stainless steel, a cobalt-chromium alloy, titanium, or a titanium alloy, but is not limited thereto. It would also be possible for the electrically conductive material of which the housing 912 and/or the housing 922 is made to be a currently developed or future developed electrically conductive polymeric material. Since the housings 912 and 922 are each made of an electrically conductive material, they can also be referred to as electrically conductive housings 912 and 922.

As shown in FIG. 9A, electronic circuitry 914 (also referred to as electronics) is included within the housing 912, and a battery 924 (e.g., the battery 114 in FIG. 1B) is located within the housing 922. The electronic circuitry 912 can include, e.g., one or more pulse generators, one or more sense amplifiers, switches, a controller, memory, and/or the like. Such a controller can include one or more processors, and/or an application-specific integrated circuit (ASIC), but is not limited thereto. Exemplary details of the electronic circuitry 912 were discussed above with reference to FIG. 1B, and are also discussed below with reference to FIG. 11. Since the electronic circuitry 912 can likely be made smaller in size that the battery 924 (which should preferably power the LP for a few years), it is likely that the housing 924 which encases the battery 924 is larger in volume than the housing 912 which encases the electronic circuitry 914. The housings 912 and 922 are preferably hermetic housings that protect the electronic circuitry 914 and the battery 924 from the harsh environment of the human body.

Still referring to FIG. 9A, an inter-housing insulator 932 is located between the housing 912 and the housing 922 to electrically isolate the housings 912 and 914 from one another. The inter-housing insulator 932 can be made, e.g., of sapphire, ruby, a biocompatible glass (e.g., borosilicate glass) or a biocompatible ceramic, but is not limited thereto. Exemplary biocompatible ceramics include, but is not limited to aluminum nitride (AlN), zirconia (ZrO2), silicon carbide (SiC), and silicon nitride (Si3N4).

In certain embodiments each of the housings 912 and 922 has a generally cylindrical shape. As shown in FIG. 9A, each of the housings 912 and 922 has an end that is connected to the inter-housing insulator 932, and an opposing end that can be referred to as the "free end" of the respective housing. The end of each housing 912 and 922 that is not the free end can be referred to as the "non-free end". The non-free end of the housing 912 can be physically attached to a first side of the inter-housing insulator 932. Similarly, the non-free end of the housing 922 can be physically attached to a second side of the inter-housing insulator 932. Where each of the housings 912 and 922 has a generally cylindrical shape the inter-housing insulator may have an annular shape or a disk-like shape, but is not limited thereto. For more specific examples, the inter-housing insulator 932 can be an annular shaped ceramic or glass collar.

Preferably there is a hermetic bonding between the non-free end of the housing 912 and the first side of the inter-housing insulator 932, and a hermetic bonding between the non-free end of the housing 922 and the second side of the inter-housing insulator 932. For example, fusion welding methods, such as laser welding, tungsten inert gas welding (TIG), or electron-beam welding can be used to hermetically bond ends of each of the first and second housings 912 and 922 to the first and second sides of the inter-housing insulator 932. In certain embodiments, multiple hermetic seals are provided between an end of a housing (912 or 922) and a side of the inter-housing insulator. Such hermetic seals can include, e.g., one or more glass-to-tantalum seals produced by melting glass with an infrared laser beam, and one or more hermetic seals obtained by melting a tantalum tube closed in a plasma needle arc welder, but are not limited thereto.

The battery 924 can be any one of various different types of batteries, such as, but not limited to, a lithium battery, e.g., a lithium carbon monofluoride (Li-CFx) battery. The use of other types of batteries is also possible and within the scope of the embodiments described herein. The battery 924 has a positive (+) pole and a negative (−) pole. In accordance with certain embodiments where the battery 924 is an Li-CFx battery, lithium (Li) provides the anode or negative (−) pole of the battery, and carbon monofluoride (CFx) provides the cathode or positive (+) pole of the battery. When referring to the battery 924, the positive (+) pole can also be referred to as the positive (+) terminal, and the negative (−) pole can also be referred to as the negative (−) terminal.

In accordance with certain embodiments, the negative (−) pole of the battery 924 is connected to the electrically conductive housing 922 that encases the battery 924. The connection between the negative (−) pole of the battery 924 and the electrically conductive housing 924 can be via a wire or other electrical conductor. Alternatively, the battery 924 can be designed and manufactured such that the outer-casing of the battery 924 is electrically connected to the negative (−) pole of the battery, or more generally, provides the negative (−) pole for the battery. Where the outer-casing of the battery 924 provides the negative (−) pole of the battery, then the negative (−) pole of the battery 924 will be connected to the electrically conductive housing 922 so long as the outer-casing of the battery 924 is physically in contact with the electrically conductive housing 922. Unless stated otherwise, it will be assumed that the outer-casing of the battery 924 provides the negative (−) pole of the battery. However, it should be noted that in alternative embodiments the battery 924 can be designed and manufactured such that the outer-casing of the battery 924 is electrically connected to the positive (+) pole of the battery, or more generally, provides the positive (+) pole for the battery.

Conductors 934 and 936 that extend through the inter-housing insulator 932 connect the positive (+) and negative (−) poles of the battery 924 to the electronics 914, which are encased within the electrically conductive housing 912, to thereby enable the battery 924 to provide power to the electronics 914.

The LP 902*a* is shown as including a tip electrode 908 that is located adjacent to the free end of the housing 912. The tip electrode 908 is electrically isolated from the electrically conductive housing 912 by an insulator 906. A feedthrough 908 that extends through the insulator 906 is used to connect the tip electrode 908 to the electronics 914 (e.g., one or more pulse generators and/or one or more sense amplifiers). The tip electrode 908 can have various different shapes, depending upon implementation. For example, the tip electrode 908 can have an annular shape, a semi-spherical cap, or a helical shape to enable the tip electrode 908 to also function as an attachment mechanism for attaching the LP 902 to an interior or exterior wall of a cardiac chamber. Where the tip electrode 908 has a helical shape it can also be referred to as a helical or helix electrode. Other shapes for the tip electrode 908 are also possible and within the embodiments of the present technology described herein.

The LP 902*a* is also shown as including a ring electrode 918 and a ring electrode 928. In certain embodiments, the ring electrode 918 is provided by a non-insulated portion of the electrically conductive housing 912. More specifically, portions of the electrically conductive housing 912 can be coated or otherwise covered by an insulator 916, and a non-insulated portion of the housing 912 can provide the ring electrode 918. Similarly, the ring electrode 928 can be provided by a non-insulated portion of the electrically conductive housing 922. More specifically, portions of the electrically conductive housing 922 can be coated or otherwise covered by an insulator 926, and a non-insulated portion of the housing 922 can provide the ring electrode 928. Such insulators 916 and 926 can be made various different types of biocompatible insulating materials, such as, but not limited to, ceramic, polyurethane, parylene, or silicone.

Where the outer-casing of the battery 924 provides the negative (−) pole of the battery, and the outer-casing of the battery 924 is physically in contact with the electrically conductive housing 922, then the electrically conductive housing 922 is electrically connected to the negative (−) pole (aka the negative terminal) of the battery 924. When using such a battery 924, an advantage of having the inter-housing insulator 932 electrically isolate the housings 912 and 922 from one another is that a single common feedthrough (936 in FIG. 9A) can be used to connect the electronics 914 to the negative (−) pole of the battery 924 and the ring electrode 928. A further advantage of having the inter-housing insulator 932 electrically isolate the housings 912 and 922 from one another is that a non-insulated portion of each of the housings can be used to provide respective ring electrodes 918 and 928. Another advantage of having the inter-housing insulator 932 electrically isolate the housings 912 and 922 from one another is that the ring electrodes 918 and 928 can be used independently of one another. Further, it is noted that designing an LP to include three electrodes should enable better sensing of far-field signals, compared to if the LP included only two electrodes.

In accordance with certain embodiments, during pacing of a cardiac chamber (e.g., RA chamber or RV chamber) within or on which the LP 902*a* is implanted, the tip electrode 908 is connected as the cathode and one of the ring electrodes 918 or 928 is connected as the anode. In other words, a tip-to-ring pacing vector can be used for pacing. It would also be possible that when performing pacing using the tip electrode 908 as the cathode, both ring electrodes 918 and 928 can be connected as the anode (e.g., a distributed anode) at the same time. In accordance with certain embodiments, sensing can be performed using one or more pair of the electrodes 902, 918, and 928. Additionally, i2i communication can be performed using a pair of the electrodes 902, 918, and 928.

In an embodiment, if the LP 902*a* is implanted within the RV chamber, then near-field sensing (of electrical cardiac activity associated with the RV chamber) can be performed using the tip electrode 908 and the ring electrode 918. In other words, a tip-to-ring sensing vector can be used for near-field sensing. In an embodiment, if the LP 902*a* is implanted in the RV chamber, then far-field sensing (of electrical cardiac activity associated with the RA chamber) can be performed using the tip electrode 908 and the ring electrode 928, since the ring electrode 928 will be the electrode closest to the RA chamber. In other words, a separate tip-to-ring sensing vector can be used for far-field sensing than is used for near-field sensing. In still another embodiment, if the LP 902*a* is implanted in the RV chamber, far-field sensing (of electrical cardiac activity associated with the RA chamber) can be performed using the ring electrode 918 and the ring electrode 928. In other words, a ring-to-ring sensing vector can be used for far-field sensing. The tip electrode 908 and the ring electrode 928 can be used for i2i communication (both transmitting of i2i pulses and receiving of i2i pulses) with another LP, another IMD, and/or with an external device (e.g., programmer). Alternatively, the tip electrode 908 and the ring electrode 918 can be used for i2i communication (both transmitting of i2i pulses and receiving of i2i pulses) with another LP, another IMD, and/or with an external device. In still other embodiments, the ring electrode 918 and the ring electrode 928 can be used for i2i communication (both transmitting of i2i pulses and receiving of i2i pulses) with another LP, another IMD, and/or with an external device.

In an embodiment, if the LP 902*a* is implanted within the RA chamber, then near-field sensing (of electrical cardiac activity associated with the RA chamber) can be performed using the tip electrode 908 and the ring electrode 918 (i.e., a tip-to-ring sensing vector can be used for near-field sensing); far-field sensing (of electrical cardiac activity associated with the RV chamber) can be performed using the tip electrode 908 and the ring electrode 928 (since the ring electrode 928 will be the electrode closest to the RV chamber) or using the ring electrode 918 and the ring electrode 928; and the tip electrode 908 and one of the ring electrodes 918 or 928 can be used for i2i communication (both transmitting of i2i pulses and receiving of i2i pulses) with another LP, another IMD, and/or with an external device, or the two ring electrode 918 and 928 can be used for i2i communication.

More generally, when the LP 902*a* is implanted within a cardiac chamber, near-field sensing (of electrical cardiac activity associated with the local chamber within which the LP 902a is implanted) can be performed using the tip electrode 908 and the ring electrode 918 (i.e., a tip-to-ring sensing vector can be used for near-field sensing); far-field sensing (of electrical cardiac activity associated with a remote chamber) can be performed using the tip electrode 908 and the ring electrode 928, or using the ring electrode 918 and the ring electrode 928; and i2i communication can be performed using the tip electrode 908 and one of the ring electrodes 918 or 928, or using both ring electrode 918 and 928. Other variations are also possible and within the scope of the embodiments of the present technology.

Still referring to FIG. 9A, the LP 902a is also shown as including a retrieval feature 942, which can include a "button" or circular grasping feature that is configured to dock within a docking cap or a retrieval catheter that can be used to remove the LP 902a when it needs to be removed and/or replaced. Alternative form factors for the retrieval feature are also possible. The retrieval feature 942 can be made of a non-electrically conductive material, i.e., an insulating material. Alternatively, the retrieval feature 942 can be made of an electrically conductive material, and in the embodiment of FIG. 9A, can be coated or otherwise covered by a biocompatible insulating materials, such as, but not limited to, ceramic, polyurethane, parylene, or silicone.

FIG. 9B is an illustration of a leadless pacemaker (LP) 902b according to another embodiment of the present technology. Elements in FIG. 9B that are the same or similar to elements in FIG. 9A are numbered the same and need not be described again in the same amount of detail. In accordance with certain embodiments, the retrieval feature 942 (or at least a portion thereof) is made of an electrically conductive material and is electrically connected to the negative (−) pole of the battery 924. This enables the retrieval feature 942 (or at least a portion thereof) to be another tip electrode 948. Accordingly, the LP 902b includes the tip electrode 908 adjacent to the free end of the housing 912, as well as a tip electrode adjacent to the free end of the housing 922. Where the retrieval feature 942 provides a tip electrode 948, it can also be referred to as the tip electrode 942/948. A comparison between FIGS. 9A and 9B shows that a distinction of the LP 902b is that instead of having one tip electrode and two ring electrodes, as was the case with the LP 902a, the LP 902b has two tip electrodes and one ring electrode. It would also be possible that a portion of the free end of the housing 922 is not coated or otherwise covered with an insulated material to thereby provide a tip electrode adjacent to the free end of the housing 922. This would also provide the LP 902b with two tip electrodes and one ring electrode.

In accordance with certain embodiments, during pacing of a cardiac chamber (e.g., RA chamber or RV chamber) within or on which the LP 902b is implanted, the tip electrode 908 is connected as the cathode and the ring electrodes 918 is connected as the anode. In other words, a tip-to-ring pacing vector can be used for pacing. In accordance with certain embodiments, sensing can be performed using one or more pair of the electrodes 902, 918, and 948. Additionally, i2i communication can be performed using a pair of the electrodes 902, 918, and 948.

In an embodiment, if the LP 902b is implanted within the RV chamber, then near-field sensing (of electrical cardiac activity associated with the RV chamber) can be performed using the tip electrode 908 and the ring electrode 918. In other words, a tip-to-ring sensing vector can be used for near-field sensing. In an embodiment, if the LP 902b is implanted in the RV chamber, then far-field sensing (of electrical cardiac activity associated with the RA chamber) can be performed using the tip electrode 908 and the tip electrode 948, since the tip electrode 948 will be the electrode closest to the RA chamber. In other words, a tip-to-tip sensing vector can be used for far-field sensing. In still another embodiment, if the LP 902b is implanted in the RV chamber, far-field sensing (of electrical cardiac activity associated with the RA chamber) can be performed using the ring electrode 918 and the tip electrode 948. In other words, a ring-to-tip sensing vector can be used for far-field sensing. The tip electrode 908 and the tip electrode 948 can be used for i2i communication (both transmitting of i2i pulses and receiving of i2i pulses) with another LP, another IMD, and/or for implant to programmer (i2p) communication with an external device. Alternatively, the ring electrode 918 and the tip electrode 948 can be used for i2i communication (both transmitting of i2i pulses and receiving of i2i pulses) with another LP, another IMD, and/or for i2p communication with an external device.

In an embodiment, if the LP 902b is implanted within the RA chamber, then near-field sensing (of electrical cardiac activity associated with the RA chamber) can be performed using the tip electrode 908 and the ring electrode 918 (i.e., a tip-to-ring sensing vector can be used for near-field sensing); far-field sensing (of electrical cardiac activity associated with the RV chamber) can be performed using the tip electrode 908 and the tip electrode 948 (since the tip electrode 948 will be the electrode closest to the RV chamber) or using the ring electrode 918 and the tip electrode 948. The tip electrode 908 and the tip electrode 948, or the ring electrode 918 and the tip electrode 948, can be used for i2i communication (both transmitting of i2i pulses and receiving of i2i pulses) with another LP, another IMD, and/or for i2p communication with an external device.

More generally, when the LP 902b is implanted within a cardiac chamber, near-field sensing (of electrical cardiac activity associated with the local chamber within which the LP 902b is implanted) can be performed using the tip electrode 908 and the ring electrode 918 (i.e., a tip-to-ring sensing vector can be used for near-field sensing); far-field sensing (of electrical cardiac activity associated with a remote chamber) can be performed using the tip electrode 908 and the tip electrode 948, or using the ring electrode 918 and the tip electrode 948; and i2i communication can be performed using the tip electrode 908 and the tip electrode 948, or using the ring electrode 918 and the tip electrode 948. Other variations are also possible and within the scope of the embodiments of the present technology.

Referring briefly back to FIG. 1B, only one sense amplifier 132 was shown within the LP illustrated therein. In accordance with certain embodiments, an LP (e.g., 102, 104, 902a or 902b) includes multiple sense amplifier, e.g., one or more for sensing near-field signals, one or more for sensing far-field signals, and one or more for sensing i2i signals. In FIG. 1B only one pulse generator 116 was shown within the LP illustrated therein. In accordance with certain embodiments, an LP (e.g., 102, 104, 902a or 902b) includes multiple pulse generators, e.g., one for generating pacing signals, and one or more for generating i2i signals. Further, it should be noted that where an LP (e.g., 102, 104, 902a or 902b) includes three or more electrodes, switch circuitry can be located between the electrodes and the sense amplifier(s) and pulse generator(s), to enable a controller to control which electrodes are used to sense a near-field signal, which electrodes are used to sense a far-field signal, which electrodes are used for pacing, and to control which electrodes are used for i2i communications.

Figure 10A:
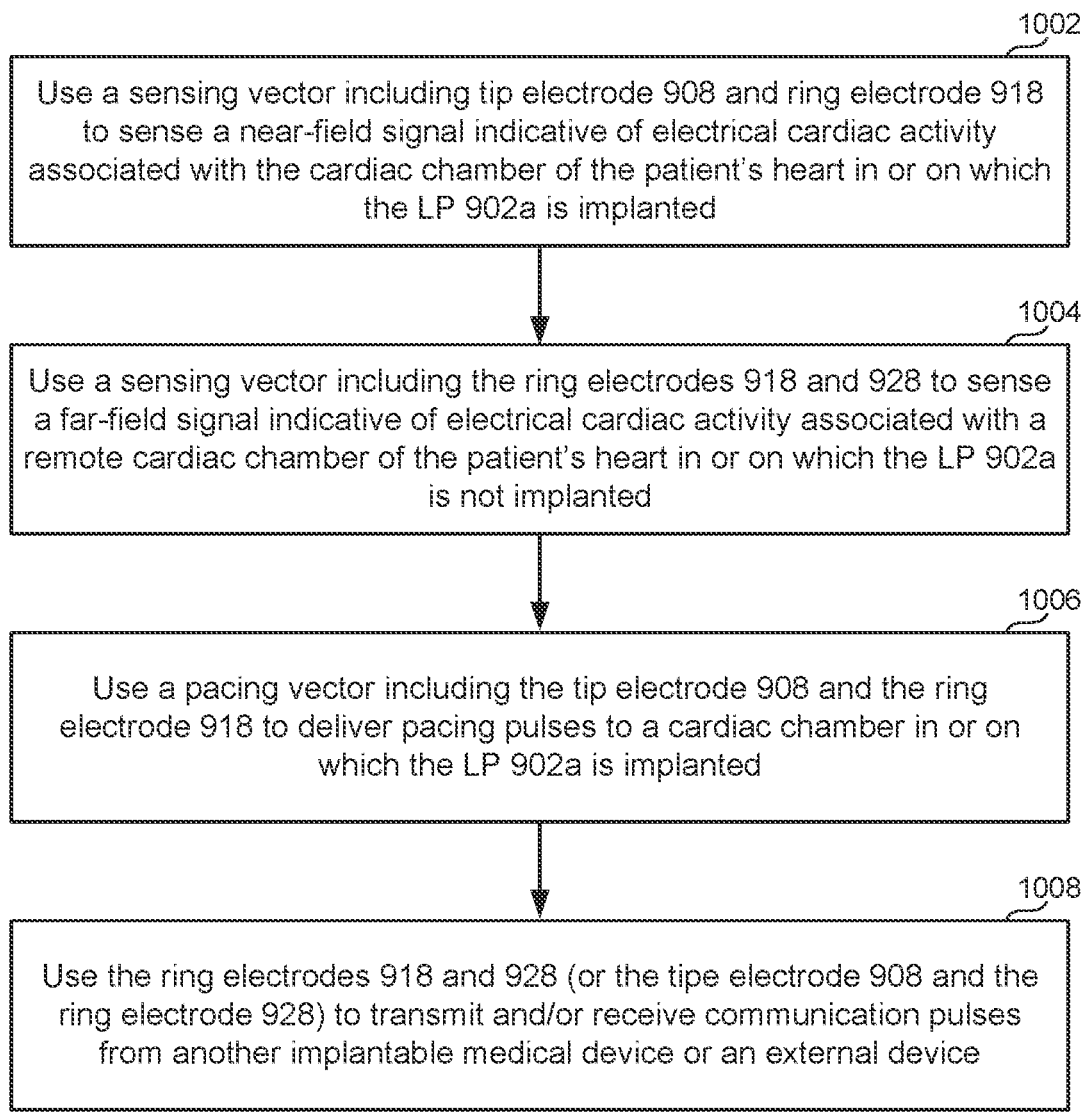
FIG. 10A is a high level flow diagram that is used to summarize certain methods of the present technology that can be used with the LP illustrated in FIG. 9A.

The high level flow diagram in FIG. 10A will now be used to summarize certain embodiments of the present technology that can be used with the LP 902a described above with reference to FIG. 9A. Referring briefly back to FIG. 9A, the LP 902a was shown as including three electrodes, including a tip electrode 908, a first ring electrode 918, and a second ring electrode 928. The electronic circuitry 914 within the housing 912 can include one or more pulse generators, one or more sense amplifiers, and a controller. The battery 924 within the housing 922 provides power to the electronic circuitry via conductors that electrically couple positive and negative poles of the battery 924 within the housing 922 to the electronic circuitry 914 within the housing 912.

Referring to FIG. 10A, step 1002 involves using a sensing vector including the tip electrode 908 and the ring electrode 918 to sense a near-field signal indicative of electrical cardiac activity associated with the local cardiac chamber of the patient's heart in or on which the LP is implanted. Step 1004 involves using a sensing vector including the ring electrodes 918 and 928 to sense a far-field signal indicative of electrical cardiac activity associated with a remote cardiac chamber of the patient's heart in or on which the LP 902a is not implanted. Step 1006 involves using a pacing vector including the tip electrode 908 and the ring electrode 918 to deliver pacing pulses to the local cardiac chamber in or on which the LP 902a is implanted. Step 1006 can also involve timing delivery of the pacing pulses based on the near-field signal (sensed at step 1002) and/or based on the far-field signal (sensed at step 1004). Step 1008 involves using the ring electrodes 918 and 928 (or the tip electrode 908 and the ring electrode 928) to transmit and/or receive communication pulses from another implantable medical device or an external device. It would also be possible to time delivery of pacing pulses (delivered at step 1006) based on i2i messages received from another implantable medical device (e.g., another LP). Depending upon the specific implementation, the order of the various steps shown in FIG. 10A can be rearranged, and thus, embodiments are not intended to be limited to the order shown in FIG. 10A. It would also be possible that just subsets of the steps shown in FIG. 10A be performed. Other variations of the methods summarized with reference to FIG. 10A could be appreciated from the above discussion of FIG. 9A.

Figure 10B:
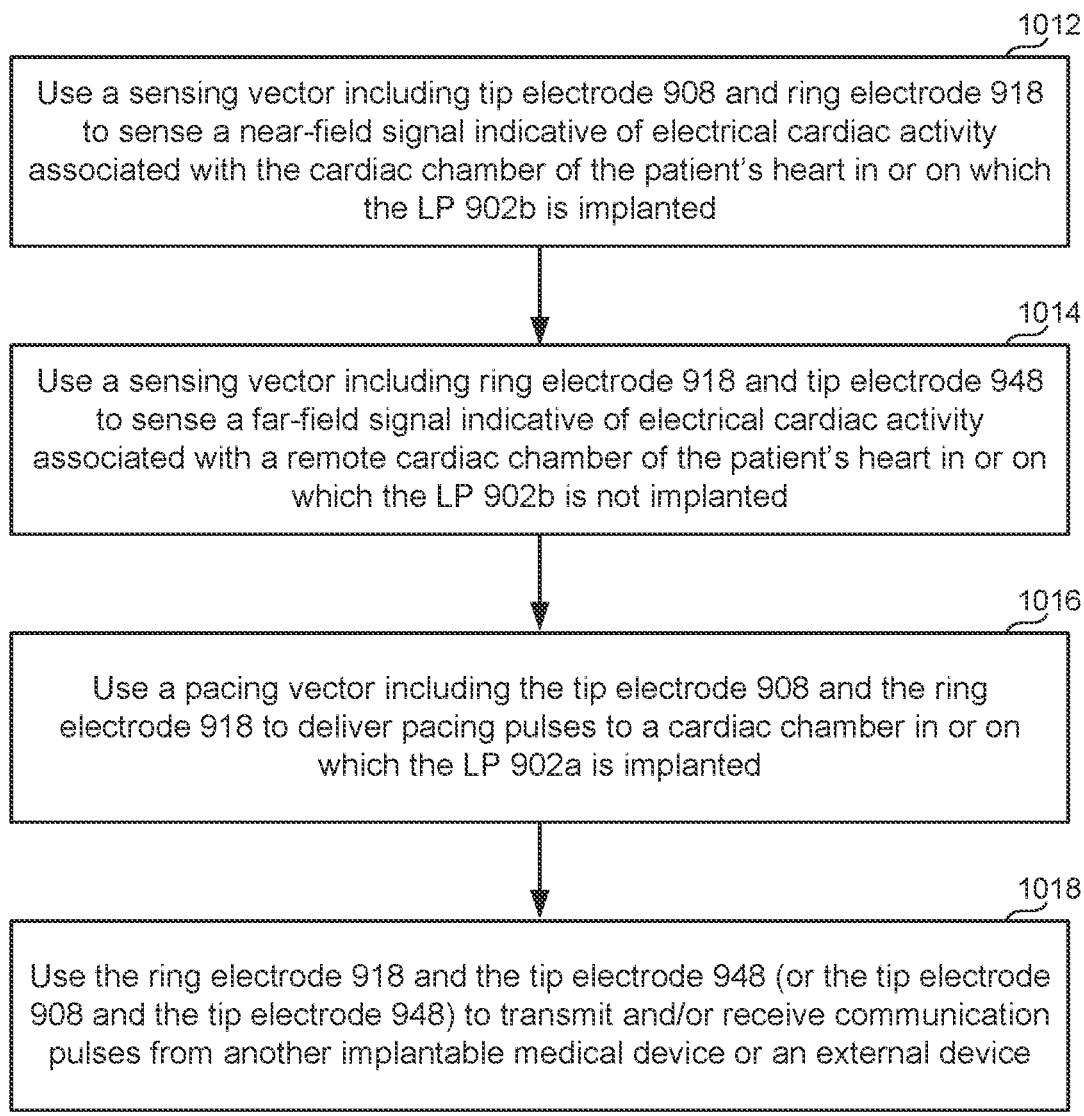
FIG. 10B is a high level flow diagram that is used to summarize certain methods of the present technology that can be used with the LP illustrated in FIG. 9B.

The high level flow diagram in FIG. 10B will now be used to summarize certain embodiments of the present technology that can be used with the LP 902b described above with reference to FIG. 9B. Referring briefly back to FIG. 9A, the LP 902b was shown as including three electrodes, including a first tip electrode 908, a ring electrode 918, and a second tip electrode 948. Again, the electronic circuitry 914 within the housing 912 can include one or more pulse generators, one or more sense amplifiers, and a controller, and the battery 924 within the housing 922 provides power to the electronic circuitry via conductors that electrically couple positive and negative poles of the battery 924 within the housing 922 to the electronic circuitry 914 within the housing 912.

Referring to FIG. 10B, step 1012 involves using a sensing vector including the tip electrode 908 and the ring electrode 918 to sense a near-field signal indicative of electrical cardiac activity associated with the local cardiac chamber of the patient's heart in or on which the LP 902b is implanted. Step 1014 involves using a sensing vector including the ring electrode 918 and the tip electrode 948 to sense a far-field signal indicative of electrical cardiac activity associated with a remote cardiac chamber of the patient's heart in or on which the LP 902b is not implanted. Step 1016 involves using a pacing vector including the tip electrode 908 and the ring electrode 918 to deliver pacing pulses to the local cardiac chamber in or on which the LP 902b is implanted. Step 1016 can also involve timing delivery of the pacing pulses based on the near-field signal (sensed at step 1012) and/or based on the far-field signal (sensed at step 1014). Step 1018 involves using the ring electrode 918 and the tip electrode 948 (or the tip electrode 908 and the tip electrode 948) to transmit and/or receive communication pulses from another implantable medical device or an external device. It would also be possible to time delivery of pacing pulses (delivered at step 1016) based on i2i messages received from another implantable medical device (e.g., another LP). Depending upon the specific implementation, the order of the various steps shown in FIG. 10B can be rearranged, and thus, embodiments are not intended to be limited to the order shown in FIG. 10B. It would also be possible that just subsets of the steps shown in FIG. 10B be performed. Other variations of the methods summarized with reference to FIG. 10B could be appreciated from the above discussion of FIG. 9B. For example, the second tip electrode 948, instead of being provided by the retrieval feature 942 (or a portion thereof), can be provided by a portion of the free end of the housing 922 that is not covered by the insulator 926.

Figure 11:
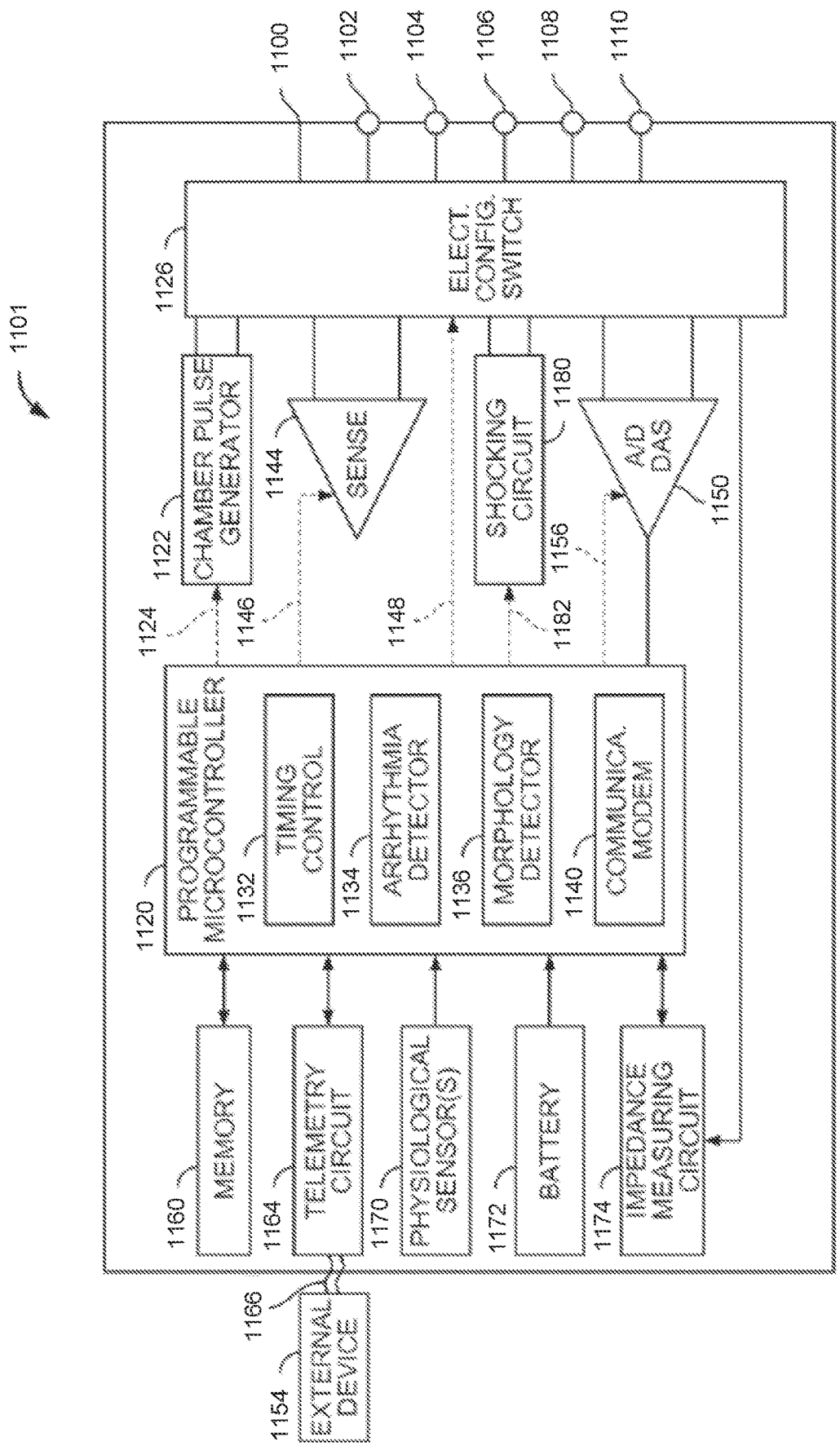
FIG. 11 shows a block diagram of an embodiment of an LP that is implanted into a patient as part of an implantable cardiac system in accordance with certain embodiments herein.

FIG. 11 shows a block diagram of showing exemplary further details of an LP 1101 (e.g., 102, 104, 902a, or 902b) that is implanted into the patient as part of the implantable cardiac system in accordance with certain embodiments herein. LP 1101 may be implemented as a full-function biventricular pacemaker, equipped with both atrial and ventricular sensing and pacing circuitry for four chamber sensing and stimulation therapy (including both pacing and shock treatment). Optionally, LP 1101 may provide full-function cardiac resynchronization therapy. Alternatively, LP 1101 may be implemented with a reduced set of functions and components. For instance, the LP may be implemented without ventricular sensing and pacing.

LP 1101 has a housing 1100 to hold the electronic/computing components. Housing 1100 (which is often referred to as the "can", "case", "encasing", or "case electrode") may be programmably selected to act as the return electrode for certain stimulus modes. Housing 1100 may further include a connector (not shown) with a plurality of terminals 1102, 1104, 1106, 1108, and 1110. The terminals may be connected to electrodes that are located in various locations on housing 1100 or elsewhere within and about the heart. LP 1101 includes a programmable microcontroller 1120 that controls various operations of LP 1101, including cardiac monitoring and stimulation therapy. Microcontroller 1120 includes a microprocessor (or equivalent control circuitry), RAM and/or ROM memory, logic and timing circuitry, state machine circuitry, and I/O circuitry. The microcontroller is an example of a controller (e.g., 112) discussed above.

LP 1101 further includes a pulse generator 1122 that generates stimulation pulses and communication pulses for delivery by one or more electrodes coupled thereto. Pulse generator 1122 is controlled by microcontroller 1120 via control signal 1124. Pulse generator 1122 may be coupled to the select electrode(s) via an electrode configuration switch 1126, which includes multiple switches for connecting the desired electrodes to the appropriate I/O circuits, thereby facilitating electrode programmability. Switch 1126 is controlled by a control signal 1128 from microcontroller 1120.

In FIG. 11, a single pulse generator 1122 is illustrated. Optionally, the LP may include multiple pulse generators, similar to pulse generator 1122, where each pulse generator is coupled to one or more electrodes and controlled by microcontroller 1120 to deliver select stimulus pulse(s) to the corresponding one or more electrodes. For example, one pulse generator can be used to generate pacing pulses, and another pulse generator can be used to generate i2i pulses.

Microcontroller 1120 is illustrated as including timing control circuitry 1132 to control the timing of the stimulation pulses (e.g., pacing rate, atrio-ventricular (AV) delay, atrial interconduction (A-A) delay, or ventricular interconduction (V-V) delay, etc.). Timing control circuitry 1132 may also be used for the timing of refractory periods, blanking intervals, noise detection windows, evoked response windows, alert intervals, marker channel timing, and so on. Microcontroller 1120 may also have an arrhythmia detector 1134 for detecting arrhythmia conditions and a morphology detector 1136. Although not shown, the microcontroller 1120 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

LP 1101 is further equipped with a communication modem (modulator/demodulator) 1140 to enable wireless communication with the remote slave pacing unit. Modem 1140 may include one or more transmitters and one or more receivers as discussed herein in connection with FIG. 1B. In one implementation, modem 1140 may use low or high frequency modulation. As one example, modem 1140 may transmit i2i messages and other signals through conductive communication between a pair of electrodes. Modem 1140 may be implemented in hardware as part of microcontroller 1120, or as software/firmware instructions programmed into and executed by microcontroller 1120. Alternatively, modem 1140 may reside separately from the microcontroller as a standalone component.

LP 1101 includes a sensing circuit 1144 selectively coupled to one or more electrodes, that perform sensing operations, through switch 1126 to detect the presence of cardiac activity associated with one or more chambers of the heart. Sensing circuit 1144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1126 determines the sensing polarity of the cardiac signal by selectively closing the appropriate switches. In this way, the clinician may program the sensing polarity independent of the stimulation polarity.

The output of sensing circuit 1144 is connected to microcontroller 1120 which, in turn, triggers or inhibits the pulse generator 1122 in response to the presence or absence of cardiac activity. Sensing circuit 1144 receives a control signal 1146 from microcontroller 1120 for purposes of controlling the gain, threshold, polarization charge removal circuitry (not shown), and the timing of any blocking circuitry (not shown) coupled to the inputs of the sensing circuitry.

In FIG. 11, a single sensing circuit 1144 is illustrated. Optionally, the LP may include multiple sensing circuits, similar to sensing circuit 1144, where each sensing circuit is coupled to one or more electrodes and controlled by microcontroller 1120 to sense electrical activity detected at the corresponding one or more electrodes. For example, one sensing circuit can be used to sense near-field signals, another sensing circuit can be used to sense far-field signals, and one or more further sensing circuits can be used to sense i2i signals.

LP 1101 further includes an analog-to-digital (A/D) data acquisition system (DAS) 1150 coupled to one or more electrodes via switch 1126 to sample cardiac signals across any pair of desired electrodes. Data acquisition system 1150 is configured to acquire intracardiac electrogram signals, convert the raw analog data into digital data, and store the digital data for later processing and/or telemetric transmission to an external device 1154 (e.g., a programmer, local transceiver, or a diagnostic system analyzer). Data acquisition system 1150 is controlled by a control signal 1156 from the microcontroller 1120.

Microcontroller 1120 is coupled to a memory 1160 by a suitable data/address bus. The programmable operating parameters used by microcontroller 1120 are stored in memory 1160 and used to customize the operation of LP 1101 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 1101 may be non-invasively programmed into memory 1160 through a telemetry circuit 1164 in telemetric communication via communication link 1166 with external device 1154. Telemetry circuit 1164 allows intracardiac electrograms and status information relating to the operation of LP 1101 (as contained in microcontroller 1120 or memory 1160) to be sent to external device 1154 through communication link 1166.

LP 1101 can further include magnet detection circuitry (not shown), coupled to microcontroller 1120, to detect when a magnet is placed over the unit. A magnet may be used by a clinician to perform various test functions of LP 1101 and/or to signal microcontroller 1120 that external device 1154 is in place to receive or transmit data to microcontroller 1120 through telemetry circuits 1164.

LP 1101 can further include one or more physiological sensors 1170. Such sensors are commonly referred to as "rate-responsive" sensors because they are typically used to adjust pacing stimulation rates according to the exercise state of the patient. However, physiological sensor 1170 may further be used to detect changes in cardiac output, changes in the physiological condition of the heart, or diurnal changes in activity (e.g., detecting sleep and wake states). Signals generated by physiological sensors 1170 are passed to microcontroller 1120 for analysis. Microcontroller 1120 responds by adjusting the various pacing parameters (such as rate, AV Delay, V-V Delay, etc.) at which the atrial and ventricular pacing pulses are administered. While shown as being included within LP 1101, physiological sensor(s) 1170 may be external to LP 1101, yet still be implanted within or carried by the patient. Examples of physiologic sensors might include sensors that, for example, sense temperature, respiration rate, pH of blood, ventricular gradient, activity, position/posture, minute ventilation (MV), and so forth. The physiological sensors 1170 can include, e.g., an accelerometer (e.g., 154 in FIG. 1B) and/or a pressure sensor (e.g., 156 in FIG. 1B).

A battery 1172 provides operating power to all of the components in LP 1101. Battery 1172 is preferably capable of operating at low current drains for long periods of time. Battery 1172 also desirably has a predictable discharge characteristic so that elective replacement time can be detected. As one example, LP 1101 employs a lithium carbon monofluoride (Li—CFx) battery. In certain embodiments, examples of which were described above with reference to FIGS. 9A and 9B, the battery 1172 (which was labeled 924 in FIGS. 9A and 9B) can be located in a first hermetic electrically conductive housing, and the microcontroller 1120 and other circuitry can be located in a second hermetic electrically conductive housing.

LP 1101 further includes an impedance measuring circuit 1174, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1174 is coupled to switch 1126 so that any desired electrode may be used. In this embodiment LP 1101 further includes a shocking circuit 1180 coupled to microcontroller 1120 by a data/address bus 1182.

In some embodiments, an LP is configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 6, 7, 8, 10A and 10B. For another example, it is possible to change the boundaries of some of the dashed blocks shown in FIGS. 1B and 11.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable system, comprising:
   a first leadless pacemaker (LP1) configured to be implanted in or on a first chamber of a heart; and
   a second leadless pacemaker (LP2) configured to be implanted in or on a second chamber of the heart;
   the LP1 configured to sense a far-field or sensor signal from which electrical or mechanical cardiac activity associated with the second chamber of the heart may be detected by the LP1 itself;
   the LP1 configured to transmit implant-to-implant (i2i) messages to the LP2, and configured to receive i2i messages from the LP2;
   the LP2 configured to receive i2i messages from the LP1, and configured to transmit i2i messages to the LP1;
   the LP1 including a controller configured to
      determine when the LP1 successfully detects electrical or mechanical cardiac activity associated with the second chamber of the heart based on the far-field or sensor signal;

determine when the LP1 fails to successfully detect the electrical or mechanical cardiac activity associated with the second chamber of the heart based on the far-field or sensor signal;

time delivery of one or more pacing pulses delivered to the first chamber of the heart by the LP1, based on timing of electrical or mechanical cardiac activity associated with the second chamber of the heart detected from the far-field or sensor signal that is sensed by the LP1 itself, when the LP1 successfully detects the electrical or mechanical cardiac activity associated with the second chamber of the heart based on the far-field or sensor signal; and time delivery of one or more pacing pulses delivered to the first chamber of the heart by the LP1, based on timing of cardiac activity associated with the second chamber of the heart as determined by the LP1 based on one or more i2i messages received from the LP2, when the LP1 fails to successfully detect the electrical or mechanical cardiac activity associated with the second chamber of the heart based on the far-field or sensor signal.

2. The implantable system of claim 1, wherein:
the LP1 is configured to be implanted in or on a right ventricular (RV) chamber; and
the LP2 is configured to be implanted in or on a right atrial (RA) chamber.

3. The implantable system of claim 2, wherein:
the LP1 is configured to perform at least one of VVI, VDI or VDD pacing;
the LP2 is configured to perform at least one of AAI, ADI or ADD pacing; and
the LP1 and the LP2 collectively providing DDD or DDI pacing or some other dual chamber pacing mode that provides synchronization between the LP1 and the LP2.

4. The implantable system of claim 1, wherein:
the LP1 is configured to be implanted in or on a right atrial (RA) chamber; and
the LP2 is configured to be implanted in or on a right ventricular (RV) chamber.

5. The implantable system of claim 4, wherein:
the LP1 is configured to perform at least one of AAI, ADI or ADD pacing;
the LP2 is configured to perform at least one of VVI, VDI or VDD pacing; and
the LP1 and the LP2 collectively providing DDD or DDI pacing or some other dual chamber pacing mode that provides synchronization between the LP1 and the LP2.

6. The implantable system of claim 1, wherein:
the LP1 includes electrodes and a sense circuit that are collectively configured to sense the far-field signal from which the electrical cardiac activity associated with the second chamber of the heart may be detected by the LP1 itself; and
the controller of the LP1 is configured to
determine when the LP1 successfully detects electrical cardiac activity associated with the second chamber of the heart based on the far-field signal;
determine when the LP1 fails to successfully detect the electrical cardiac activity associated with the second chamber of the heart based on the far-field signal;
time delivery of the one or more pacing pulses delivered by the LP1 to the first chamber of the heart, based on the timing of the electrical cardiac activity associated with the second chamber of the heart detected by the LP1 itself from the far-field signal, when the LP1 successfully detects the electrical cardiac activity associated with the second chamber of the heart based on the far-field signal; and
time delivery of one or more pacing pulses delivered to the first chamber of the heart by the LP1, based on timing of cardiac activity associated with the second chamber of the heart as determined by the LP1 based on one or more i2i messages received from the LP2, when the LP1 fails to successfully detect the electrical cardiac activity associated with the second chamber of the heart based on the far-field signal.

7. The implantable system of claim 1, wherein:
the LP1 includes a sensor configured to sense the sensor signal from which the mechanical cardiac activity associated with the second chamber of the heart may be detected by the LP1 itself; and
the controller of the LP1 is configured to
determine when the LP1 successfully detects mechanical cardiac activity associated with the second chamber of the heart based on the sensor signal;
determine when the LP1 fails to successfully detect the mechanical cardiac activity associated with the second chamber of the heart based on the sensor signal;
time delivery of the one or more pacing pulses delivered by the LP1 to the first chamber of the heart, based on the timing of the mechanical cardiac activity associated with the second chamber of the heart detected by the LP1 itself from the sensor signal, when the LP1 successfully detects the mechanical cardiac activity associated with the second chamber of the heart based on the sensor signal; and
time delivery of one or more pacing pulses delivered to the first chamber of the heart by the LP1, based on timing of cardiac activity associated with the second chamber of the heart as determined by the LP1 based on one or more i2i messages received from the LP2, when the LP1 fails to successfully detect the mechanical cardiac activity associated with the second chamber of the heart based on the sensor signal.

8. The implantable system of claim 7, wherein the sensor of the LP1 comprises an accelerometer or a pressure sensor.

9. The implantable system of claim 1, wherein:
the LP2 is configured to sense a second far-field or sensor signal from which electrical or mechanical cardiac activity associated with the first chamber of the heart may be detected by the LP2 itself;
the LP2 includes a second controller configured to
determine when the LP2 successfully detects electrical or mechanical cardiac activity associated with the first chamber of the heart based on the second far-field or sensor signal;
determine when the LP2 fails to successfully detect the electrical or mechanical cardiac activity associated with the first chamber of the heart based on the second far-field or sensor signal;
time delivery of one or more pacing pulses delivered to the second chamber of the heart by the LP2, based on timing of electrical or mechanical cardiac activity associated with the first chamber of the heart detected from the far-field or sensor signal that is sensed by the LP2 itself, when the LP2 successfully detects the electrical or mechanical cardiac activity associated with the first chamber of the heart based on the second far-field or sensor signal; and
time delivery of one or more pacing pulses delivered to the second chamber of the heart by the LP2, based on timing of cardiac activity associated with the first chamber of the heart as determined by the LP2 based on one or more i2i messages received from the LP1, when the LP2 fails to successfully detect the electrical or mechanical cardiac activity associated with the first chamber of the heart based on the second far-field or sensor signal.

10. A method for use with an implantable system including a first leadless pacemaker (LP1) configured to be implanted in or on a first chamber of a heart, and a second leadless pacemaker (LP2) configured to be implanted in or on a second chamber of the heart, the method comprising:

the LP1 transmitting implant-to-implant (i2i) messages to the LP2, and receiving i2i messages from the LP2;

the LP2 receiving i2i messages from the LP1, and transmitting i2i messages to the LP1;

the LP1 sensing a far-field or sensor signal from which electrical or mechanical cardiac activity associated with the second chamber of the heart may be detected by the LP1 itself; and a controller of the LP1 determining when the LP1 successfully detects electrical or mechanical cardiac activity associated with the second chamber of the heart based on the far-field or sensor signal;

determining when the LP1 fails to successfully detect the electrical or mechanical cardiac activity associated with the second chamber of the heart based on the far-field or sensor signal;

timing delivery of one or more pacing pulses delivered to the first chamber of the heart by the LP1, based on timing of electrical or mechanical cardiac activity associated with the second chamber of the heart detected from the far-field or sensor signal that is sensed by the LP1 itself, during a first period of time when the LP1 successfully detects the electrical or mechanical cardiac activity associated with the second chamber of the heart based on the far-field or sensor signal; and timing delivery of one or more pacing pulses delivered to the first chamber of the heart by the LP1, based on timing of cardiac activity associated with the second chamber of the heart as determined by the LP1 based on one or more i2i messages received from the LP2, during a second period of time when the LP1 fails to successfully detect the electrical or mechanical cardiac activity associated with the second chamber of the heart based on the far-field or sensor signal.

11. The method of claim 10, wherein the first chamber comprises a right ventricular (RV) chamber, the second chamber comprises a right atrial (RA) chamber, the LP1 is configured to be implanted in or on the RV chamber, and the LP2 is configured to be implanted in or on the RA chamber, and wherein:

the controller of the LP1 timing delivery of the one or more pacing pulses delivered by the LP1 to the RV chamber of the heart during the first period of time comprises the LP1 timing delivery of the one or more pacing pulses delivered by the LP1 to the RV chamber based on the timing of the electrical or mechanical cardiac activity associated with the RA chamber, detected by the LP1 itself, based on the far-field signal obtained using electrodes of the LP1 or the sensor signal obtained using a sensor of the LP1, during the first period of time when the LP1 successfully detects the electrical or mechanical cardiac activity associated with the second chamber of the heart based on the far-field or sensor signal; and the controller of the LP1 timing delivery of the one or more pacing pulses delivered by the LP1 to the RV chamber of the heart during the second period of time comprises the LP1 timing delivery of the one or more pacing pulses delivered by the LP1 to the RV chamber based on the timing of cardiac activity associated with the RA chamber as determined based on one or more i2i messages received by the LP1 from the LP2, during the second period of time when the LP1 fails to successfully detect the electrical or mechanical cardiac activity associated with the RA chamber of the heart based on the far-field or sensor signal.

12. The method of claim 11, wherein the far-field or sensor signal that is sensed by the LP1 comprises a far-field signal sensed using electrodes of the LP1.

13. The method of claim 11, wherein the far-field or sensor signal that is sensed by the LP1 comprises a sensor signal sensed using a sensor of the LP1.

14. The method of claim 10, wherein the first chamber comprises a right atrial (RA) chamber, the second chamber comprises a right ventricular (RV) chamber, the LP1 is configured to be implanted in or on the RA chamber, and the LP2 is configured to be implanted in or on the RV chamber, and wherein:

the controller of the LP1 timing delivery of the one or more pacing pulses delivered by the LP1 to the RA chamber of the heart during the first period of time comprises the LP1 timing delivery of the one or more pacing pulses delivered by the LP1 to the RA chamber based on the timing of the electrical or mechanical cardiac activity associated with the RV chamber, detected by the LP1 itself, based on the far-field signal obtained using electrodes of the LP1 or the sensor signal obtained using a sensor of the LP1, during the first period of time when the LP1 successfully detects the electrical or mechanical cardiac activity associated with the RV chamber of the heart based on the far-field or sensor signal; and the controller of the LP1 timing delivery of the one or more pacing pulses delivered by the LP1 to the RA chamber of the heart during the second period of time comprises the LP1 timing delivery of the one or more pacing pulses delivered by the LP1 to the RA chamber based on the timing of cardiac activity associated with the RV chamber as determined based on one or more i2i messages received by the LP1 from the LP2, during the second period of time when the LP1 fails to successfully detect the electrical or mechanical cardiac activity associated with the RV chamber of the heart based on the far-field or sensor signal.

15. The method of claim 14, wherein the far-field or sensor signal that is sensed by the LP1 comprises a far-field signal sensed using electrodes of the LP1.

16. The method of claim 14, wherein the far-field or sensor signal that is sensed by the LP1 comprises a sensor signal sensed using a sensor of the LP1.

17. The method of claim 10, further comprising:
the LP2 sensing a second far-field or sensor signal from which electrical or mechanical cardiac activity associated with the first chamber of the heart may be detected by the LP2 itself;
a second controller of the LP2
- determining when the LP2 successfully detects electrical or mechanical cardiac activity associated with the first chamber of the heart based on the second far-field or sensor signal;
- determine when the LP2 fails to successfully detect the electrical or mechanical cardiac activity associated with the first chamber of the heart based on the second far-field or sensor signal;
- timing delivery of one or more pacing pulses delivered to the second chamber of the heart by the LP2, based on timing of electrical or mechanical cardiac activity associated with the first chamber of the heart detected from the second far-field or sensor signal that is sensed by the LP2 itself, during a period of time when the LP2 successfully detects the electrical or mechanical cardiac activity associated with the first chamber of the heart based on the second far-field or sensor signal; and
- timing delivery of one or more pacing pulses delivered to the second chamber of the heart by the LP2, based on timing of cardiac activity associated with the first chamber of the heart as determined by the LP2 based on one or more i2i messages received from the LP1, during a further period of time when the LP2 fails to successfully detect the electrical or mechanical cardiac activity associated with the first chamber of the heart based on the second far-field or sensor signal.

18. A leadless pacemaker, comprising:
a housing configured to be implanted in or on a first chamber of a heart;
electrodes, at least one of which can be provided by a portion of the housing;
a telemetry circuit within the housing and configured to transmit implant-to-implant (i2i) messages to, and receive i2i messages from, another leadless pacemaker that is configured to be implanted in or on a second chamber of the heart;
a pulse generator within the housing and configured to generate pacing pulses that can be delivered to the first chamber of the heart via the electrodes; and
a controller within the housing;
wherein the electrodes of the leadless pacemaker, or a sensor of the leadless pacemaker, can be used to sense a far-field or sensor signal from which electrical or mechanical cardiac activity associated with the second chamber of the heart may be detected by the leadless pacemaker itself; and
wherein the controller is configured to
- determine when electrical or mechanical cardiac activity associated with the second chamber of the heart is successfully detected based on the far-field or sensor signal;
- determine when the electrical or mechanical cardiac activity associated with the second chamber of the heart is not successfully detected based on the far-field or sensor signal;
- time delivery of one or more of the pacing pulses delivered to the first chamber of the heart via the electrode, based on timing of electrical or mechanical cardiac activity associated with the second chamber of the heart detected from the far-field or sensor signal that is sensed by the leadless pacemaker itself, when the electrical or mechanical cardiac activity associated with the second chamber of the heart is successfully detected based on the far-field or sensor signal; and
- time delivery of one or more pacing pulses delivered to the first chamber of the heart via the electrodes, based on timing of cardiac activity associated with the second chamber of the heart as determined based on one or more i2i messages received from the other leadless pacemaker, when the electrical or mechanical cardiac activity associated with the second chamber of the heart is not successfully detected based on the far-field or sensor signal.

19. The leadless pacemaker of claim 18, wherein the far-field or sensor signal that is sensed by the leadless pacemaker comprises a far-field signal sensed using electrodes of the leadless pacemaker.

20. The leadless pacemaker of claim 18, wherein the far-field or sensor signal that is sensed by the leadless pacemaker comprises a sensor signal sensed using a sensor of the leadless pacemaker.

21. The leadless pacemaker of claim 20, wherein the sensor of the leadless pacemaker comprises an accelerometer or a pressure sensor.

22. The leadless pacemaker of claim 18, wherein:
the first chamber of the heart comprises the right ventricular (RV) chamber and the second chamber of the heart comprise the right atrial (RA) chamber; or
the first chamber of the heart comprises the RA chamber and the second chamber of the heart comprise the RV chamber.

* * * * *